US009889222B2

(12) United States Patent
Song

(10) Patent No.: US 9,889,222 B2
(45) Date of Patent: Feb. 13, 2018

(54) AQUEOUS MEDIUM-SENSITIVE COATING COMPOSITIONS FOR TRIGGERED RELEASE OF ACTIVE INGREDIENTS AND VISUAL INDICATION FOR WETNESS

(71) Applicant: Kimberly-Clark Worldwide, Inc., Neenah, WI (US)

(72) Inventor: Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 951 days.

(21) Appl. No.: 14/356,547

(22) PCT Filed: Nov. 7, 2012

(86) PCT No.: PCT/US2012/063821
§ 371 (c)(1),
(2) Date: May 6, 2014

(87) PCT Pub. No.: WO2013/070674
PCT Pub. Date: May 16, 2013

(65) Prior Publication Data
US 2014/0324004 A1    Oct. 30, 2014

Related U.S. Application Data

(63) Continuation-in-part of application No. 13/292,612, filed on Nov. 9, 2011, now Pat. No. 8,791,045.

(51) Int. Cl.
*A61F 13/42* (2006.01)
*A61L 15/56* (2006.01)
(Continued)

(52) U.S. Cl.
CPC .............. *A61L 15/56* (2013.01); *A61F 13/42* (2013.01); *B32B 5/022* (2013.01); *B32B 5/26* (2013.01);
(Continued)

(58) Field of Classification Search
CPC .......... A61F 13/42; A61F 2013/421–2013/429
(Continued)

(56) References Cited

U.S. PATENT DOCUMENTS 4,020,156 A    4/1977  Murray et al.
4,880,921 A    11/1989 Bodor
(Continued)

FOREIGN PATENT DOCUMENTS

EP    0 752 465 A1    1/1997
EP    0 771 785 B1    1/2002
(Continued)

OTHER PUBLICATIONS

Co-pending U.S. Appl. No. 14/066,856, filed Oct. 30, 2013, by Song et al. for "Triggerable Compositions for Two-Stage, Controlled Release of Proactive Chemistry."

*Primary Examiner* — Susan Su
(74) *Attorney, Agent, or Firm* — Kimberly-Clark Worldwide, Inc.

(57) ABSTRACT

An absorbent article includes a topsheet layer, a backsheet layer and one absorbent core layer. The topsheet layer, absorbent core layer and backsheet layer each include a longitudinally directed side peripheral edge. The absorbent article further includes an aqueous medium-sensitive coating composition for triggered release of active ingredients from the absorbent article. The aqueous medium-sensitive coating composition is affixed to the absorbent article adjacent a longitudinally directed side peripheral edge. The coating composition includes a betaine ester or betaine ester derivative having a functional active group derived from a fragrance with a hydroxyl group, a color changing visual indicator chemistry, where the visual indicator chemistry is
(Continued)

selected from at least one of the group of a pH indicator dye and pH adjuster, a thermochromic dye and a polarity-sensitive dye.

21 Claims, 6 Drawing Sheets

(51) Int. Cl.
- C09D 11/50 (2014.01)
- G01N 31/22 (2006.01)
- G01N 21/29 (2006.01)
- B32B 5/02 (2006.01)
- B32B 5/26 (2006.01)

(52) U.S. Cl.
CPC ............. *C09D 11/50* (2013.01); *G01N 21/29* (2013.01); *G01N 31/222* (2013.01); *A61F 2013/422* (2013.01); *A61F 2013/427* (2013.01); *B32B 2255/02* (2013.01); *B32B 2255/26* (2013.01); *B32B 2262/0253* (2013.01); *B32B 2307/4026* (2013.01); *B32B 2307/726* (2013.01); *B32B 2555/00* (2013.01); *B32B 2555/02* (2013.01)

(58) Field of Classification Search
USPC .................................................. 604/359, 361
See application file for complete search history.

(56) References Cited

U.S. PATENT DOCUMENTS

| | | | |
|---|---|---|---|
| 5,130,290 A | 7/1992 | Tanimoto | |
| 5,133,958 A | 7/1992 | Stuckler | |
| 5,197,958 A | 3/1993 | Howell | |
| 5,389,093 A | 2/1995 | Howell | |
| 5,622,944 A | 4/1997 | Hale et al. | |
| 5,827,913 A | 10/1998 | Baetzold et al. | |
| 5,958,870 A * | 9/1999 | Declercq | C11D 1/46 510/102 |
| 6,369,290 B1 | 4/2002 | Glaug et al. | |
| 6,458,456 B1 | 10/2002 | Zainiev et al. | |
| 6,586,639 B2 | 7/2003 | Murayama et al. | |
| 6,677,297 B2 | 1/2004 | Frerot | |
| 7,056,878 B2 | 6/2006 | Fender et al. | |
| 7,105,715 B2 | 9/2006 | Carlucci et al. | |
| 7,229,958 B2 | 6/2007 | Koehle et al. | |
| 7,407,670 B2 | 8/2008 | Six et al. | |
| 7,501,536 B2 | 3/2009 | Jaunky et al. | |
| 7,550,416 B2 | 6/2009 | Woo et al. | |
| 7,655,830 B2 | 2/2010 | Flohr et al. | |
| 7,758,888 B2 | 7/2010 | Lapidot et al. | |
| 8,022,030 B2 | 9/2011 | Berthier et al. | |
| 9,371,464 B2 * | 6/2016 | Breton | C09D 11/38 |
| 2003/0083513 A1 | 5/2003 | Murayama et al. | |
| 2005/0131363 A1 | 6/2005 | Kim et al. | |
| 2005/0256479 A1 | 11/2005 | Giovanni et al. | |
| 2007/0021319 A1 | 1/2007 | Kohle et al. | |
| 2007/0031485 A1 | 2/2007 | Ljusberg-Wahren et al. | |
| 2007/0081953 A1 | 4/2007 | Dahms | |
| 2007/0105793 A1 | 5/2007 | Hendrix | |
| 2007/0160553 A1 | 7/2007 | Kripp et al. | |
| 2007/0270773 A1 | 11/2007 | Mackey | |
| 2008/0139378 A1 | 6/2008 | Hildebrand et al. | |
| 2008/0279253 A1 | 11/2008 | MacDonald et al. | |
| 2008/0286224 A1 | 11/2008 | Vega et al. | |
| 2009/0054860 A1 | 2/2009 | Young et al. | |
| 2009/0156634 A1 | 6/2009 | Molino et al. | |
| 2009/0221980 A1 | 9/2009 | Mosbacher et al. | |
| 2009/0275908 A1 | 11/2009 | Song | |
| 2010/0012017 A1 | 1/2010 | Miller | |
| 2010/0030173 A1 | 2/2010 | Song et al. | |
| 2010/0160299 A1 | 6/2010 | Baker, Jr. et al. | |
| 2010/0221330 A1 | 9/2010 | Messadek | |
| 2010/0227896 A1 | 9/2010 | Biedermann et al. | |
| 2010/0248959 A1 | 9/2010 | Kato et al. | |
| 2010/0307422 A1 | 12/2010 | Huck et al. | |
| 2011/0015599 A1 | 1/2011 | Song et al. | |
| 2011/0046571 A1 | 2/2011 | Waldhorn | |
| 2011/0104023 A1 | 5/2011 | Nakatsubo et al. | |
| 2011/0144603 A1 | 6/2011 | Song | |
| 2011/0152805 A1 | 6/2011 | Gil | |
| 2011/0250286 A1 | 10/2011 | Marcello et al. | |
| 2012/0064136 A1 | 3/2012 | Baker, Jr. et al. | |
| 2012/0121669 A1 | 5/2012 | Fontana et al. | |
| 2012/0259098 A1 | 10/2012 | Baker, Jr. et al. | |
| 2013/0018076 A1 | 1/2013 | Friedel et al. | |
| 2013/0066289 A1 | 3/2013 | Song et al. | |
| 2013/0116644 A1 | 5/2013 | Wei et al. | |
| 2014/0128827 A1 | 5/2014 | Song | |

FOREIGN PATENT DOCUMENTS

| | | |
|---|---|---|
| JP | 01-275511 A | 11/1989 |
| JP | 03-221039 A | 9/1991 |
| WO | WO 1998/026808 A2 | 6/1998 |
| WO | WO 2001/027234 A1 | 4/2001 |
| WO | WO 2003/047558 A2 | 6/2003 |
| WO | WO 2008/068059 A2 | 6/2008 |
| WO | WO 2009/018368 A1 | 2/2009 |
| WO | WO 2010/088053 A2 | 8/2010 |
| WO | WO 2012/094636 A2 | 7/2012 |
| WO | WO 2013/016257 A1 | 1/2013 |

* cited by examiner

AQUEOUS MEDIUM-SENSITIVE COATING COMPOSITIONS FOR TRIGGERED RELEASE OF ACTIVE INGREDIENTS AND VISUAL INDICATION FOR WETNESS

This application is a continuation-in-part application claiming priority from presently copending U.S. application Ser. No. 13/292,612 entitled "Non-Tacky Wetness Indicator Composition For Application On a Polymeric Substrate" filed on Nov. 9, 2011, in the names of Ning Wei et al.

FIELD OF INVENTION

The present invention pertains to wetness indicators involving either a visual color changing effect, or an olfactory change in response to the presence of an aqueous-based liquid. In particular, the invention relates to chemical compositions for providing such visual or olfactory wetness signals, as well as absorbent articles having such wetness indicators attached thereto or incorporated therein, that communicate to a caregiver or product-user that the article either is ready for immediate changing, or will need to be replaced shortly.

BACKGROUND

The ability of a disposable absorbent article to sense wetness, soiling, or a change of condition has been routinely recognized by manufacturers, as a desirable feature for a variety of modern hygiene products. Disposable absorbent articles such as infant (baby care) and child care diapers, and training pants; adult incontinence pads, pants and briefs; feminine sanitary products such as pads, napkins, tampons, and liners; wiping products; bed liners and the like, are highly absorbent and efficiently pull moisture away from a surrounding environment. However, given these products' ability to absorb large quantities of aqueous liquid, they may easily become saturated, much to the surprise of a product user or caregiver.

In the case of disposable personal care absorbent articles which are to be worn next to a user's body, reducing skin irritation caused by prolonged wetness exposure is of utmost concern. Because these articles are so absorbent, wearers or caregivers may also not realize the products have been soiled, particularly if the topsheet facing the user, and of which a caregiver touches during use, may appear dry. If users are inexperienced toddlers or incapacitated individuals who may not recognize the meaning of body sensations associated with urination or soiling, they may also not be able to appreciate that a product needs to be changed. In any event, the saturation of such absorbent products may also eventually lead to product leakage and subsequently, to embarrassing garment odors and unsightly stains.

In the case of discreet absorbent articles that cannot be easily viewed by a consumer during product usage, except by undressing (such as sanitary napkins), consumers may further not appreciate the actual saturation level of a product, ahead of an imminent leakage event. Thus, the caregiver or wearer may not recognize that the article is ready to be replaced or that leakage may shortly occur. Leakage from such discreet products may result in undergarment, outergarment or bedding stains.

Visual indicator mechanisms have therefore been employed by consumer absorbent product manufacturers for some time, to signal the presence of wetness or a change in condition of the absorbent articles. See for example, JP2000-279442, which describes a color changing ink. A large number of wetness sensing and visual indicator technologies currently exist, including electronic-based wetness sensors, ink-based color changing wetness indicators, enzyme or other chemical-based sensors which change appearance upon a change in chemistry within a product, pH change-based indicators, and temperature change-based wetness indicators. Such wetness indicators each typically provide visual or audible indication of article soiling by a color changing, a color disappearing or a color appearing, or by the emission of a sound. Such wetness indicators may simply consist of water soluble inks which disappear upon contact with liquid moisture.

Much of the heretofore described wetness sensing and signalling technology is frequently impractical for implementation in absorbent articles, as the technology is too expensive to implement on relatively lower-cost products. Further, certain chemistries, such as enzyme-based wetness sensors, may have stability issues. Water-soluble, dye-based wetness indicators also often lack the high detection sensitivity desirable for use in new-born diapers. They also may provide poor color contrast which sometimes makes signal reading difficult. There is therefore a need for a practical, sensitive wetness indicator technology that can be easily implemented in a wide array of absorbent articles.

While certain color changing ink-based sensing technology has advanced, and is affordable for large scale absorbent article implementation, such technology may not be as effective for certain absorbent article applications in which the physical location of a user and placement of the article prevents the easy checking of a visual sensor. For example, while color changing ink-based wetness indicators may easily be used for situations in which a user is confined to a bed or other location looked after by a caregiver, or where the article is readily visible, such as on the exposed diaper of a sleeping or crawling infant or walking toddler, such technology offers less advantages for feminine care absorbent articles, or for adult care absorbent articles to be used by active adults, which are not readily visible and for which discretion is of the utmost user concern.

Olfactory or fragrance-based wetness indicators have also been described to provide an alternative to visual indication of article soiling. For example, olfactory wetness signals are described in US2009/0221980 to Mosbacher et al. Such reference describes the use of malodorous materials in an absorbent article, as well as the use of volatile esters to provide a pleasant aromatic scent upon the degrading of encapsulation materials or a storage pouch by liquid moisture, the encapsulation or pouch materials being used to contain the volatile fragrance within the absorbent article.

Fragrances are also frequently described for general use in absorbent articles to mask the body odors of sweat, urine, menses or bowel movements. However, fragrance indicators and masking components are often unstable due to their inherent volatility, such as being derived from essential oils. Such chemistry often demonstrates short shelf lives and as a result, presents packaging, manufacturing, and extended use concerns. There is therefore a need for olfactory wetness indicators that do not solely rely on encapsulation or storage containers (at added cost). There is a further need for such indicators that have prolonged shelf-lives.

In an attempt to provide a controlled odor masking effect over urine in disposable sanitary products, US2008/0139378 to Hildebrand et al., describes the use of non-volatile organopolysiloxane formulations to deliver odor control functionality. Upon contact with urine, a fragrance alcohol is released by acid-catalyzed hydrolysis of betaine functional groups carrying a radical of a fragrance alcohol on the organopolysiloxane molecule. As noted in the reference, the release of a fragrance alcohol occurs selectively upon contact with acidic urine. Such functional groups are described as being more stable against hydrolysis at a neutral pH. Therefore, use of such high molecular weight chemistry in neutral or non-acidic environments is not described as delivering fragrance functionality, and no other indicator technology is described as useful with such chemistry. Furthermore organopolysiloxane chemistry is often used to impart hydrophobic attributes to products. As such, it poses use challenges within absorbent articles, in that the hydrophobic chemistry significantly impacts aqueous-based liquid flow and absorption pathways. Such organopolysiloxane chemistry includes large polymer molecules, which are often costly and may be difficult to place in solution. A need therefore exists for a controlled odor masking system that is readily released upon occurrence of a soiling event (not the result of a relatively slow hydrolysis reaction), which does not significantly hinder absorbency pathways, and which is readily soluble.

To combine numerous sensing technologies or wetness indicator technologies with other chemical functionality is cost prohibitive, and presents practical challenges in disposable absorbent article manufacture. Furthermore, the separate implementation of odor masking/signaling chemistry and visual wetness indicating/coating technology adds additional manufacturing steps as well. A need therefore exists, for signaling technology for disposable absorbent articles which can provide multisensory wetness and absorbent capacity signals to consumers, and which also masks body exudate odors.

Thus, a need exists for a coating chemistry technology that is of relatively low cost, and easy to be implemented in the manufacture of absorbent products, and which may be capable of being combined with other chemical functionality to achieve enhanced benefits, such as capacity indicators. A need also exists for a relatively stable wetness indicator composition which offers multiple signals in a single composition to a caregiver or consumer, that is not limited in its triggerability by pH chemistry of wetness, and which is not hindered by the normally short shelf life common to volatile fragrances and essential oils. Finally, a need also exists for indicator composition systems which offer relatively less interference with absorbency channels in an absorbent article.

SUMMARY OF THE INVENTION

In general, the present disclosure is directed to a multisensory, aqueous medium-sensitive coating composition, which can be used to coat various portions of an absorbent article for the later purpose of wetness and capacity indication. Such coating composition provides both visual and olfactory warning of article soiling and/or impending article leakage. At the same time, such coating provides odor masking upon an article's soiling by aqueous-based bodily fluids such as urine, vaginal secretions, menses, mucous or loose bowel movements, or alternatively from household spills containing liquid water.

In one embodiment of the invention, an aqueous medium-sensitive coating composition for triggered release of active ingredients and visual indication of the presence of aqueous medium from absorbent articles includes a betaine ester or betaine ester derivative including a fragrance radical, that is derived from a fragrance alcohol with at least one hydroxyl group. The composition further includes a visual, color changing wetness indicator, which changes color from a first color to a second color upon a change of condition, wherein the visual, color changing wetness indicator includes at least one of a pH indicator dye and pH adjuster, a thermochromic dye, and a polarity-sensitive dye. In an alternative of this composition, the aqueous medium-sensitive coating composition includes at least a pH indicator dye and a pH adjuster as the color changing chemistry. In yet a further alternative of this composition, the active ingredient is a fragrance radical group on the betaine ester or betaine ester derivative, derived from a volatile fragrance alcohol, which radical is released from the betaine ester or betaine ester derivative through a hydrolysis reaction upon contact with an aqueous medium. In yet a further alternative embodiment of the composition, the fragrance radical is derived from the group of fragrances selected from thymol, vanillin, menthol and eugenol. In yet a further alternative embodiment of the composition, the composition includes at least a pH indicator dye, a pH adjuster, a surfactant, and a binder.

In still a further alternative embodiment, the composition is applied to an absorbent article. In another alternative embodiment, the composition is applied to an absorbent article which includes at least a topsheet layer, backsheet layer and absorbent core layer between the topsheet layer and backsheet layer, and further wherein the coating composition is applied to at least one of the topsheet layer, backsheet layer and absorbent core layer within the absorbent article. In yet a further alternative embodiment, the absorbent article is either a feminine care article, a baby and child care article, an adult incontinence article or an absorbent sheet cleaning article. In still a further alternative embodiment, the coated absorbent article includes at least one peripheral side edge and the coating composition is located adjacent the at least one peripheral side edge. In another alternative embodiment, the layers within the absorbent article each include at least one peripheral side edge and the coating composition is applied onto at least one layer at a location that is adjacent a peripheral side edge. In still a further alternative embodiment of the invention, the coated absorbent article includes at least a single absorbent core layer, wherein the absorbent core layer includes the coating composition.

In still a further alternative embodiment of the invention, the coated absorbent article includes an absorbent core layer having a peripheral side edge and the coating composition is applied or affixed to the absorbent core layer at least adjacent the peripheral side edge. In yet another alternative embodiment, the absorbent article and topsheet layer, backsheet layer and absorbent core layer include a central insult deposition zone (in a crotch region) and a peripheral side edge, and the coating composition is deposited to at least one of the central insult deposition zone and the peripheral side edge.

In still a further alternative embodiment of the invention, a coated absorbent article includes at least a topsheet layer, a backsheet layer and an absorbent core layer, wherein the wetness indicator coating composition is applied to at least one of the topsheet layer, backsheet layer and absorbent core layer. In yet another alternative embodiment of the invention, a coated absorbent article includes a peripheral side edge and the wetness indicator coating composition is applied to a portion of the absorbent article adjacent the peripheral side edge.

In still another alternative embodiment of the invention, the coated absorbent article includes a topsheet layer, backsheet layer and absorbent core layer, with each layer include at least one peripheral side edge, and the wetness indicating coating composition is applied adjacent to at least one peripheral side edge of either the topsheet layer, backsheet layer or absorbent core layer. In still a further alternative embodiment of the invention, the wetness indicator coating composition includes a color changing pH indicator dye, a pH adjuster, and a betaine ester or betaine ester derivative with a functional active derived from a fragrance having at least one hydroxyl group. Alternatively, the coating composition includes a solvent, surfactant and binder.

In yet another alternative embodiment of the invention, an absorbent article coated with the composition includes at least two separated coating applications. In still a further alternative embodiment of the invention, the two separated coating applications are on two different layers within the absorbent article. In still another alternative embodiment of the invention, the coated absorbent article includes longitudinally directed side peripheral edges and front and back end peripheral side edges and the coating composition is applied adjacent at least one of the longitudinally directed side peripheral edges and front and back end peripheral edges. In another alternative embodiment, the coating composition is applied adjacent of two longitudinally directed side peripheral edges and the front and back end peripheral edges.

In another alternative embodiment of the invention, an absorbent article includes at least one absorbent core layer, wherein the absorbent article includes at least one longitudinally directed side peripheral edge. The absorbent article includes an aqueous medium-sensitive coating composition for triggered release of active ingredients from the absorbent article, with the aqueous medium-sensitive coating composition affixed to the absorbent article adjacent the longitudinally directed side peripheral edge. The coating composition includes a betaine ester or betaine ester derivative including a functional active group; and a color changing visual indicator chemistry, wherein the color changing visual indicator chemistry is selected from at least one of the group of, a pH indicator dye and pH adjuster, a thermochromic dye, and a polarity-sensitive dye.

In yet another alternative embodiment of the invention, an absorbent article includes at least a topsheet layer, a backsheet layer and one absorbent core layer. The topsheet layer, absorbent core layer and backsheet layer each include a longitudinally directed side peripheral edge. The absorbent article includes an aqueous medium-sensitive coating composition for triggered release of active ingredients from the absorbent article. The aqueous medium-sensitive coating composition is affixed to the absorbent article adjacent at least one of the longitudinally directed side peripheral edges and includes a betaine ester or betaine ester derivative including a functional active group derived from a fragrance with a hydroxyl group; a color changing visual indicator chemistry, wherein the visual indicator chemistry is selected from at least one of the group selected from a pH indicator dye and pH adjuster, a thermochromic dye and a polarity-sensitive dye.

Other features and aspects of the present disclosure are discussed in greater detail below.

Figure 1:
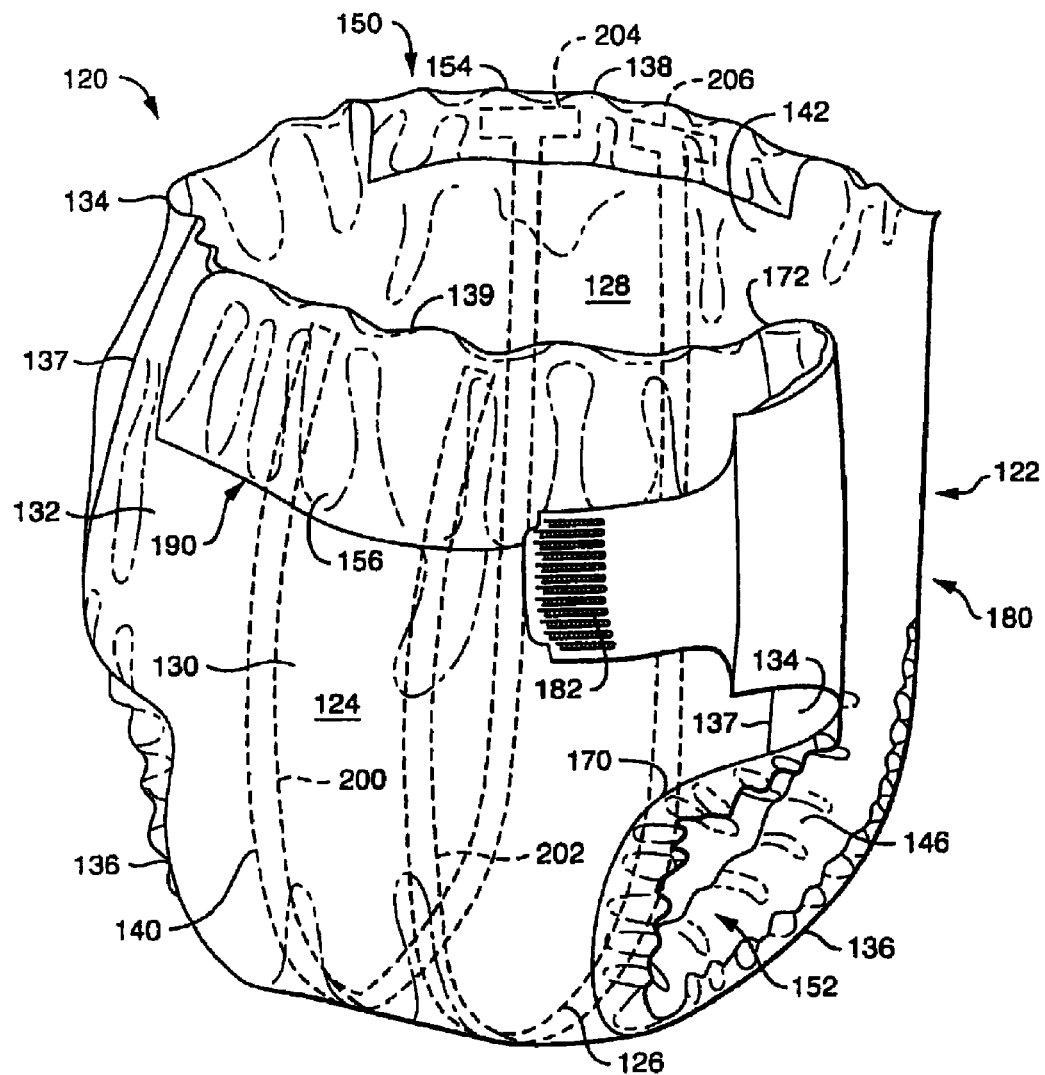
FIG. 1 is a rear perspective view of an embodiment of an absorbent article having multisensory wetness-signaling indicators according to the invention, the article in the form of an unfastened diaper.

It is to be noted that repeat use of reference characters in the present specification and drawings is intended to represent same or analogous features or elements of the disclosure.

DETAILED DESCRIPTION OF THE INVENTION

In general, the present invention is directed to a multisensory, aqueous medium-sensitive, coating composition for the triggered release of functional active ingredients in the form of fragrances, and for the provision of visual indication of wetness. In particular, the coating composition is for the triggered release of functional active ingredients and visual indicators from absorbent articles. Such aqueous medium-sensitive coating provides "multisensory" indication of wetness or soiling of the absorbent article through both visual and olfactory indication of wetness of the absorbent article by an aqueous fluid, such as urine, menses, vaginal secretions, mucous, or bowel movements. Depending on how such coating is utilized in an absorbent article, such coating composition can be used as both a wetness indicator/signal of initial soiling and mask of odor, as well as a capacity indicator, indicating that the absorbent article capacity has been reached or that the article faces imminent leakage.

Such coating is triggered upon contact with an aqueous medium, as opposed to moisture vapor. Therefore, it is less sensitive to triggering by mere exposure to air humidity. It is capable of being applied to an article without the need for specialized encapsulation or packaging. Further, the release of olfactory wetness signals from the coating is not slow, once an aqueous medium has contacted the coating. For the purposes of this application, the term "aqueous medium" shall mean a medium containing "liquid" water as opposed to water vapor. Such aqueous medium is exemplified by urine, vaginal fluids, mucous, menses, runny, liquid, or loose bowel movements, as well as household water-containing spills.

For the purposes of this description, such absorbent article may be a disposable personal care or consumer hygiene absorbent article. Such personal care article may be for baby (infant) or child care, such as diapers, training pants, bed pads, or wipes for example; for feminine hygiene care, such as sanitary pads, napkins, liners, tampons, or wipes for example; for adult incontinence care, such as undergarment inserts, pants, briefs, bed pads or wipes. Alternatively, such absorbent articles may be for household or personal cleaning or disinfecting, such as the absorbent sheets of tissues, towels or wipes. Additional examples of absorbent articles which may benefit from such coatings include hospital gowns, surgical drapes, and sterilization wraps.

For the purposes of this description, such coating chemistry is a singular coating chemical composition, that includes multisensory indicator components in one formula. Such multiple indicator components are multisensory, such that a user is signaled in different ways that soiling has occurred. The coating is applied to an absorbent article as a single composition rather than as multiple compositions applied at different times or in different locations. Such singular coating composition chemistry is used to provide visual wetness indicator functionality as well as odor masking or odor signaling functionality. Such singular coating composition can be applied to one or more separated areas of an absorbent article. In one embodiment, as will later be explained, it is desirable for several separate applications of such coating composition to be physically separate on a single absorbent article, such that they are adjacent various peripheral side edges of an absorbent article or layer within the absorbent article.

Such multisensory indicator compositions can be used within disposable absorbent articles, and in particular personal care absorbent articles, to also provide indication of imminent product leakage, such as by particular placement in locations within absorbent articles (or layers within articles) that would contact a liquid medium at a time prior to imminent leakage, such as at or near an article's peripheral side edges. In such an instance, the coating composition would only be activated upon initial soiling at an article's edges, or movement of liquid wetness of an aqueous medium in the article to locations adjacent an article's or article layer's peripheral side edge(s). Upon detecting of the olfactory indicator (the smell of the released volatile fragrance upon contact with liquid water), the consumer would then understand that the soiling had spread to a location in the article where leakage could shortly occur. As such, the composition would be useful as a capacity indicator, rather than merely as a soiling indicator.

For the purposes of this application, fragrances are considered functional "active" ingredients. As such, betaine esters with fragrance radicals may be considered active ingredient precursors (or profragrances). For the purposes of this application, the relevant betaine esters are altered with the addition of one or more fragrance-radical groups which, when they are released, become volatile, such as upon a dried coating composition (containing the betaine ester with fragrance radical) coming in contact with an aqueous medium. Such aqueous medium may be of any pH value, for example such as that which may be found in vaginal excretions, urine, runny feces, menses, or other body excretion, such as a nasal discharge, as well as household spills.

Such multisensory coating composition includes at least a betaine ester or betaine ester derivative with radical fragrance group, and a color changing dye, desirably a leuco dye, pH changing dye, thermochromic dye, or polarity-sensitive dye. For the purposes of this application, the term "color changing" shall refer to the change of a first color to a second color, such as from green to blue or blue to yellow, as opposed to color appearing from a previously non-colored state, or color disappearing to a non-colored state. The coating composition further desirably includes an organic solvent and optionally other components that would enhance the formulation functionality, such as for example, one or more developers (for color enhancement depending on dye or ink type), desensitizers, one or more surfactants, one or more binders, and one or more pH adjusters. Further components and additives may include ink preservatives, and ordinary additional fragrance additives as are well known in the art. Other additives may be used such as to adjust the physical properties of the composition. For example, the composition may contain reagents to adjust the viscosity of the solution, or may include chemicals to improve adhesion of the composition to certain substrate surfaces upon drying or cooling (in the case of a melt coating). The composition may further include chemistry that tailors the coating composition's subsequent wettability on the substrate surface. All of the foregoing components are desirably dissolved together in a volatile organic solvent medium to form a homogeneous solution. In other embodiments, such materials may be combined in a hot melted coating.

For the purposes of this description, a suitable betaine ester shall be described by the general formula of:

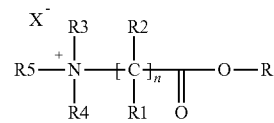

The betaine ester is an ester of betaine and a volatile fragrance with one or more hydroxyl groups. That is, the (R) group is a radical of a volatile fragrance alcohol with one or more hydroxyl groups. Desirably, the (R) moiety is independently derived from a fragrance alcohol of more than four (4) carbon atoms of synthetic or natural origin; each R1, R2, R3, R4 and R5 independently is selected from hydrogen, or organic moities such as alkyl, hydroxyalkyl, aryl, or aromatic groups, with $n \geq 1$, preferably 2 or 3, and $\leq 4$, because the larger the number "n", the less likelihood of rapid hydrolysis (hence the slower the release of fragrance). Desirably in one embodiment, groups R3-R5 include less than 8 carbon atoms in totality, desirably with any one group (R3, R4 or R5) including between 2-6 carbon atoms. In one embodiment, each R3-R5 group is desirably a methyl group. X is a compatible anion. Such (R) fragrance alcohol group component includes components having odiferous properties. It should also be recognized that the larger the value for "n", the more difficult also for the betaine ester to solubilize in water as well as undergo hydrolysis. Further, the smaller the R1 thru R5 groups, the less stable the betaine ester with associated fragrance alcohol (R) is, in the sense that the more likelihood that vapor/humidity in the air alone will cause the disassociation of the fragrance alcohol group from the betaine ester molecule. Further, if the betaine ester is too hydrophobic, that is, if it includes large hydrophobic groups in the R3-R5 positions, or is part of a larger hydrophobic structure, the more likely that it will not be water soluble.

As noted, it is desirable that the betaine ester is not large, (not including an "n" number larger than 4, that it is not part of a larger polymer structure, and not itself bonded as a functional group, to a chain base structure) such that it can be easily solubilized, and not be so hydrophobic in nature that it would be difficult to process, and would impact aqueous liquid flow on a coated substrate. Further, if the betaine ester is too large, in that it includes larger groups in its R3-R5 positions, or is part of a larger structure, it has been found that the hydrolysis reaction time is slower. In a desirable embodiment, such betaine ester includes only hydrogen or alkyl carbon-based moities in its R1-R5 groups.

In one embodiment, the functional active (radical of the fragrance alcohol) of the (R) group is selected from the fragrance group comprising 4-allyl-2-methoxyphenol (eugenol), 3-(2-bornyloxy)-2-methyl-1-propanol, 2-tert-butylcyclohexanol, 4-tert-butylcyclohexanol, benzyl alcohol, 1-decanol, 9-decen-1-ol, dihydroterpineol, 2,4-dimethyl-4-cyclohexen-1-yl methanol, 2,4-dimethylcyclohexyl methanol, 2,6-dimethyl-2-heptanol, 2,6-dimethyl-4-heptanol, 3a,4,5,6,7,7a-hexahydro-2,4-dimethyl-4,7-methano[1H]inden-5-ol, 3,7-dimethyl-1,6-nonadien-3-ol, 2,6-dimethyl-2,7-octadien-6-ol (linalool), cis-3,7-dimethyl-2,6-octadien-1-ol (nerol), trans-3,7-dimethyl-2,6-octadien-1-ol (geraniol), 3,7-dimethyl-1,7-octanediol, 3,7-dimethyl-1-octanol(tetrahydrogeraniol), 2,6-dimethyl-2-octanol (tetrahydromyrcenol), 3,7-dimethyl-3-octanol (tetrahydrolinalool), 2,6-dimethyl-7-octen-2-ol (dihydromyrcenol), 3,7-dimethyl-6-octen-1-ol (citronellol), 2,2-dimethyl-3-(3-methylphenyl)-1-propanol, 2,2-dimethyl-3-phenyl-1-propanol, 2-ethoxy-4-methoxymethylphenol, 2-ethyl-4-(2,2,3-trimethyl-3-cyclopenten-1-yl)-2-buten-1-ol, cis-3-hexen-1-ol, 4-(4-hydroxy-3-methoxyphenyl)-2-butanone, 1-hydroxy-2-(1-methyl-1-hydroxyethyl)-5-methylcyclohexane, 3-(hydroxymethyl)-2-nonanone, 4-(4-hydroxy-4-methylpentyl)-3-cyclohexene-1-carboxaldehyde, isoborneol, 3-isocamphylcyclohexanol, 2-isopropenyl-5-methylcyclohexanol (isopulegol), 1-isopropyl-4-methylcyclohex-3-enol (terpinenol), 4-isopropylcyclohexanol, 1-(4-isopropylcyclohexyl) ethanol, 4-isopropylcyclohexylmethanol, 2-isopropyl-5-methylcyclohexanol (menthol), 2-isopropyl-5-methylphenol (thymol), 5-isopropyl-2-methylphenol (carvacrol), 2-(4-methyl-3-cyclohexenyl)-2-propanol (terpineol), 2-(4-methylcyclohexyl)-2-propanol (dihydroterpineol), 4-methoxybenzyl alcohol, 2-methoxy-4-methylphenol, 3-methoxy-5-methylphenol, 1-methoxy-4-propenylbenzene (anethol), 2-methoxy-4-propenylphenol (isoeugenol), 4-methyl-3-decen-5-ol, 2-methyl-6-methylene-7-octen-2-ol (myrcenol), 3-methyl-4-phenyl-2-butanol, 2-(2-methylphenyl) ethanol, 2-methyl-4-phenyl-1-pentanol, 3-methyl-5-phenyl-1-pentanol, 2-methyl-1-phenyl-2-propanol, (1-methyl-2-(1,2,2-trimethylbicyclo[3.1.0]hex-3-ylmethyl) cyclopropyl) methanol, 3-methyl-4-(2,2,6-trimethylcyclohexen-1-yl)-2-butanol, 2-methyl-4-(2,2,3-trimethyl-3-cyclopenten-1-yl)-2-buten-1-ol, (3-methyl-1-(2,2,3-trimethyl-3-cyclopentenyl)-3-cyclohexen-1-yl) methanol, 3-methyl-5-(2,2,3-trimethyl-3-cyclopenten-1-yl)-4-penten-2-ol, 2-methyl-2-vinyl-5-(1-hydroxy-1-methylethyl)tetrahydrofuran, trans,cis-2,6-nonadienol, 1-nonanol, nopol, 1,2,3,4,4a,5,6,7-octahydro-2,5,5-trimethyl-2-naphthol, 1-octanol, 3,4,5,6,6-pentamethyl-2-heptanol, 2-phenylethanol, 2-phenylpropanol, 3-phenylpropanol (hydrocinnamic alcohol), 3-phenyl-2-propen-1-ol (cinnamic alcohol), 4-(5,5,6-trimethylbicyclo[2.2.1]hept-2-yl)cyclohexan-1-ol, 3,5,5-trimethylcyclohexanol, 2,4,6-trimethyl-4-cyclohexen-1-yl-methanol, 5-(2,2,3-trimethyl-3-cyclopentenyl)-3-methylpentan-2-ol, 3,7,11-trimethyl-2,6,10-dodecatrien-1-ol (farnesol), 3,7,11-trimethyl-1,6,10-dodecatrien-3-ol (nerolidol), 3,5,5-trimethyl-1-hexanol (isononanol), 1-undecanol, 10-undecen-1-ol, vetiverol.

In another desirable embodiment, the fragrance active group (R) on the betaine ester is derived from 2-phenoxyethanol, phenylethylalcohol, geraniol, citronellol, 3-methyl-5-phenyl-1-pentanol, 2,4-dimethyl-3-cyclohexene-1-methanol, linalool, tetrahydrolinalool, 1,2-dihydromyrcenol, hydroxycitronellal, farnesol, menthol, eugenol, thymol, vanilin, cis-3-hexenol, terpineol and mixtures thereof.

An example of a particularly desirable fragrance active (R) group which is attached to the betaine ester is the radical of eugenol. Eugenol itself is represented by the following formula:

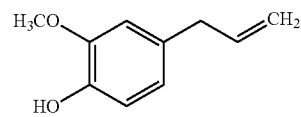

Other particularly desirable (R) groups from volatile fragrance alcohols include, radicals of menthol and thymol, with thymol offering the additional advantage of providing potential antibacterial functionality to the absorbent article on which it is coated. While such fragrance volatiles are actively volatile in their disassociated alcohol state, such volatility is eliminated once their radicals are attached as part of the betaine ester at the (R) location.

The "X" anions have no caustic or markedly irritating effect on human or animal skin, and are desirable for use in the coating, for association with the betaine ester. The anions are desirably chosen from the group comprising chloride, bromide, methyl sulfate, ethyl sulfate, sulfate, nitrate, phosphate and hydrogen phosphate.

As noted, once the betaine ester with fragrance radical moiety has been synthesized, it has been found that the (R) group is not volatile and is stable in the absence of an aqueous medium. This is especially the case for betaine esters in which R3-R5 include at least 8 carbons in total, in their structures. Following the introduction of the betaine ester or betaine ester derivative to an aqueous medium, it undergoes a hydrolysis reaction in which the fragrance separates from the betaine ester and is released as an active fragrance volatile. Such is illustrated by the following reaction:

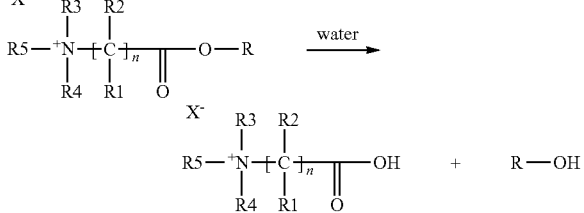

The resulting biproducts are carboxylic acid and a volatile fragrance alcohol ((R—OH) structure), with the latter released into the article surrounding environment to produce the olfactory signal.

In an alternative embodiment, the betaine ester with fragrance radical (R) may be further chemically encapsulated by a stimuli-sensitive matrix or shell, so that it is not released inadvertently, or is released intentionally more slowly, and only upon the presence of a threshhold amount of stimuli, such as a threshhold amount of aqueous medium of a certain pH level. Examples of materials for a matrix or shell include, but are not limited to water soluble polymers, pH sensitive polymers, thermogels or a combination thereof as are known in the art.

In general, betaine esters, their derivatives, and their preparation are known, and as such, the synthesis steps of particular betaine esters with fragrance radical groups will not be further delineated. However, examples of relatively smaller betaine ester molecules with attached fragrance radicals (radical groups of volatile alcohols) may be found in U.S. Pat. No. 5,958,870 to Declercq et al. and EP0752465 to Struillou, each of which are hereby incorporated by reference thereto in their entirety. It has now been found however, that such chemistry is particularly well suited as a base chemistry for a singular indicator formulation for use as both olfactory and visual wetness indicator coatings of absorbent articles, particularly if such betaine esters, are limited in size, do not necessarily require trigger by extreme pH changes, and which do not severely impact absorbency pathways, either as a result of their level of hydrophobicity or particular placement within an absorbent article.

Alternatively, such betaine esters can be used with targeted pH color changing dye indicators to create wetness and capacity indicators for specific consumer absorbent products. For example, understanding that different bodily fluids demonstrate certain pH ranges, pH sensitive visual indicators can be employed with such betaine esters in absorbent substrates such that upon soiling by aqueous-based bodily fluids, both visual and olfactory wetness indicators/capacity indicators can be triggered, offering sensitivity to a particular bodily exudate. As an example, the pH of vaginal secretions and urine very often differ, and therefore the pH indicator inks used with such betaine esters would differ to correlate with the pH of the respective bodily fluids.

Desirably, in one embodiment, the betaine ester or betaine ester derivative with attached fragrance alcohol radical, is present in the coating composition in an amount of between about 0.1 and 30% by weight, alternatively, between about 0.1 to about 20 weight %, further alternatively, between about 1 to 10 weight %, still further alternatively between about 2 and 10 weight %, still further alternatively between about 2 and 5 weight %. These weight percentages, and all weight percentages which follow, are based on the total weight of the coating composition.

The aqueous medium-sensitive, multisensory coating composition of the present invention desirably includes a nonaqueous liquid solvent or carrier for holding the betaine ester or betaine ester derivative, visual indicator dye and other formulation components, since contact with aqueous liquid will result in the hydrolysis reaction. All the components in the multisensory indicator composition are desirably soluble in the one or more volatile organic solvents, such as solvents used for flexographic and gravure printing. Suitable volatile organic solvents may include, for example, ethanol, methanol, propanol, isopropanol, butanol, acetone, butanone, tetrahydrofuran (THF), benzene and toluene, methylene chloride, chloroform, or combinations thereof. When the solution of the multisensory visual and olfactory indicator components and an organic solvent is formed, the solution is liquid at room temperature. The volatile organic solvent evaporates when the multisensory indicator composition is applied to a desired substrate. The volatile organic solvents can be present from about 20 to about 90 weight %; typically between about 25, 30, or 35 to about 60, 70, or 80 weight %, inclusive.

As such aqueous medium-sensitive coating composition is designed to present both a visual and an olfactory indication of soiling, the composition will also include an aqueous medium triggerable dye, such that appearance of aqueous medium will trigger either a change in color from a first color to a second color, an appearance of color, where previously there had been none, or the disappearance of a previously present color of the composition. In one desirable embodiment, the visual indicator is a color changing dye, that changes from a first color to a second dye. It should be appreciated however, that such olfactory indicators may suitably be used without accompanying visual indicators in targeted areas of an absorbent article, such as along an article's or layer's peripheral side edges or within noted distances from the peripheral side edge(s), so as to provide capacity indication. As an alternative, such multisensory indicator composition can be used in a first location on an absorbent article, and the same or different olfactory indicator as is included in the multisensory indicator composition may be used in a second location, closer to the peripheral edge of the article or layer in the article. In this situation, when a different smell is detected (from a different olfactory indicator), the consumer would recognize that article leakage is imminent.

Types of dyes for creating the visual change of the visual indicator that are useful in the composition include leuco dyes, pH indicator dyes, thermochromic dyes, as well as polarity-sensitive dyes. Color appearing and disappearing dyes and product designs are described for example, in U.S. Pat. No. 6,307,119 to Cammarota and US Publication 20100030173 to Song et al., each of which is incorporated by reference herein in its entirety.

In one embodiment, it is desirable for such dye to be a color appearing leuco dye. Leuco dyes are generally referred to as colorless or pale-colored basic dyes, because the dye molecules can acquire two forms, one of which is colorless. It is desirable for such leuco dyes to be used in conjunction with developers. Although not intended to be bound by theory, it is believed that a color-developer used with a leuco dye functions as a Lewis acid, which withdraws electrons from the leuco dye molecule to generate a conjugated system. Hence, the leuco dye appears to manifest color from an originally colorless state.

For example, the spiro form of an oxazine is a colorless leuco dye; the conjugated system of the oxazine and another aromatic part of the molecule is separated by an sp3-hybridized "spiro" carbon. After protonating a part of the molecule, irradiation with UV-light or introducing other kind of such change, the bond between the spiro carbon and the oxazine interrupts, the ring opens, the spiro carbon achieves sp2 hybridization and becomes planar, the aromatic group rotates, aligns its n-orbitals with the rest of the molecule, and a conjugated system forms, with the ability to absorb photons of visible light, and therefore appear colorful.

The leuco dyes that may be employed can be selected from a variety of dyes including, for example, phthalide leuco dyes, triarylmethane leuco dyes, and fluoran leuco dyes. Examples may include (1) triarylmethane-based dyes, e.g. 3,3-bis(p-dimethylaminophenyl)-6-dimethylaminophthalide, 3,3-bis(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl) phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, 3-p-dimethylaminophenyl-3-(1-methylpyrrol-3-yl)-6-dimethylaminophthalide (2) diphenylmethane-based dyes, e.g., 4,4'-bisdimethylaminobenzhydryl benzyl ether, N-halophenylleucoauramine, N-2, 4,5-trichlorophenyl-leucoauramine, etc. (3) lactam-based dyes, e.g., rhodamine-B-anilinolactam, rhodamine-(p-nitroanilino)lactam, rhodamine-(o-chloroanilino)lactam (4) Fluoran-based dyes, e.g., 3-dimethylamino-7-methoxyfluoran, 3-diethylamino-6-methoxyfluoran, 3-di-ethylamino-7-methoxyfluoran, 3-diethylamino-7-chlorofluoran, 3-diethylamino-6-methyl-7-chlorofluoran, 3-di-ethylamino-6,7-dimethylfluoran, 3-(N-ethyl-p-toluidino)-7-methylfluoran, 3-diethylamino-7-(N-acetyl-N-methylamino)fluoran, fluoran, 3-diethylamino-7-(N-methylamino)fluoran, 3-diethylamino-7-dibenzylaminofluoran, 3-diethylamino-7-(N-methyl-N-benzylamino)fluoran, 3-diethylamino-7-(N-chloroethyl-N-methylamino)fluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidino) fluoran, 3-diethylamino-6-methyl-7-phenylaminofluoran, 3-dibutylamino-6-methyl-7-phenylaminofluoran, 3-diethylamino-7-(2-carbomethoxyphenylamino) fluoran, 3-(N-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-(2,4-dimethylamino)fluoran, 3-diethylamino-7-(o-chlorophenylamino)fluoran, 3-dibutylamino-7-(o-chlorophenylamino)fluoran, 3-pyrrolidino-6-methyl-7-(p-butylphenylamino) fluoran, 3-(N-methyl-N-n-amylamino)-6-methyl-7-phenylaminofluoran, 3-(N-ethyl-N-n-amylamino)-6-methyl-7-phenylaminofluoran, 3-(N-ethyl-N-isoamylamino)-6-methyl-7-phenylaminofuluoran, 3-(N-methyl-N-n-hexylamino)-6-methyl-7-phenylaminofluoran, 3-(N-ethyl-N-n-hexylamino)-6-methyl-7-phenylaminofluoran, 3-(N-ethyl-N-β-ethylhexylamino)-6-methyl-7-phenylaminofluoran, etc. The basic dyes useful in this invention are not limited to those exemplified above, and at least two of them can be used in a mixture.

Alternatively, the visual indicator component of the multisensory indicator composition may be color-changing dye such as a pH-sensitive dye/ink employing one or more pH change dyes/chromogens to achieve a desired color changing effect. The particular chromogens employed in the pH-sensitive dye-based ink embodiment are not generally critical, unless the desire is to correlate the pH indicator dye to the presence of a specific bodily fluid. For instance, phthalein chromogens constitute one class of suitable pH-sensitive dyes that may be employed in the present disclosure. Phenol Red (i.e., phenolsulfonephthalein), for example, exhibits a transition from yellow to red over the pH range 6.6 to 8.0. Above a pH of about 8.1, Phenol Red turns a bright pink (fuchsia) color. Derivatives of Phenol Red can also be suitable for use in the present disclosure, such as those substituted with chloro, bromo, methyl, sodium carboxylate, carboxylic acid, hydroxyl and amine functional groups. Exemplary substituted Phenol Red compounds include, for instance, Metacresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',3",5',5"-tetrabromophenolsulfonephthalein), Bromochlorophenol Blue (the sodium salt of dibromo-5',5"-dichlorophenolsulfonephthalein), Bromocresol Purple (5',5"-dibromo-ortho-cresolsulfonephthalein), and Bromocresol Green (3',3",5',5"-tetrabromo-ortho-cresolsulfonephthalein). For example, Bromocresol Green exhibits a transition from yellow to blue over a pH range of about 4 to about 6; Bromothymol Blue exhibits a transition from yellow to blue over a pH range of about 6.0 to 7.6; Bromophenol Blue exhibits a transition from yellow to violet over a pH range of about 3.0 to 4.6; and Bromocresol Purple exhibits a transition from yellow to violet over a pH of about 5.2 to 6.8.

Anthraquinones constitute another suitable class of pH-sensitive dyes for use in the present disclosure. Anthraquinones have the following general structure:

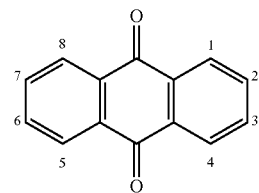 [SMILES: O=C1c2ccccc2C(=O)c2ccccc21]

The numbers 1-8 shown in the general formula represent a location on the fused ring structure at which substitution of a functional group can occur. Some examples of such functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones may be formed with varying colors and intensities. Other functional groups, such as sulfonic acids, can also be used to render certain types of compounds (e.g., higher molecular weight anthraquinones) water-soluble.

Some suitable anthraquinones that may be used in the present disclosure, as classified by their "CI" number, include Acid Black 48, Acid Blue 25 (D&C Green No. 5), Acid Blue 40, Acid Blue 41, Acid Blue 45, Acid Blue 80, Acid Blue 129, Acid Green 25, Acid Green 27, Acid Green 41, Acid Violet 43, Mordant Red 11 (Alizarin), Mordant Black 13 (Alizarin Blue Black B), Mordant Red 3 (Alizarin Red S), Mordant Violet 5 (Alizarin Violet 3R), Alizarin Complexone, Natural Red 4 (Carminic Acid), Disperse Blue 1, Disperse Blue 3, Disperse Blue 14, Natural Red 16 (Purpurin), Natural Red 8, Reactive Blue 2 (Procion Blue HB), Reactive Blue 19 (Remazol Brilliant Blue R); Alizarin, Alizarin Yellow R, Alizarin Yellow GG, Alizarin S, Nuclear Fast Red, Quinalizarin, Emodin, amino-4-hydroxyanthraquinone, and so forth. For instance, carminic acid exhibits a first transition from orange to red over a pH range of about 3.0 to 5.5 and a second transition from red to purple over a pH range of about 5.5 to 7.0.

Yet another suitable class of pH-sensitive dyes that may be employed is aromatic azo compounds having the general structure:

wherein, $R_1$ is an aromatic group;

$R_2$ is selected from the group consisting of aliphatic and aromatic groups, and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, halides, etc. Also suitable are azo derivatives, such as azoxy compounds (X—$R_1$—N=NO—$R_2$—Y) or hydrazo compounds (X—$R_1$—NH—NH—$R_2$—Y). Particular examples of such azo compounds (or derivatives thereof) include Methyl Violet, Methyl Yellow, Methyl Orange, Methyl Red, and Methyl Green. For instance, Methyl Yellow undergoes a transition from red to yellow at a pH range of about 2.9 to 4.0, Methyl Orange undergoes a transition from red to yellow at a pH range of about 3.1 to 4.4, and Methyl Red undergoes a transition from red to yellow at a pH range of about 4.2 to 6.3. Still other suitable pH-sensitive chromogens that may be employed include Congo Red, Litmus (azolitmin), Methylene Blue, Neutral Red, Acid Fuchsin, Indigo Carmine, Brilliant Green, Picric acid, Metanil Yellow, m-Cresol Purple, Quinaldine Red, Tropaeolin OO, 2,6-dinitrophenol, Phloxine B, 2,4-dinitrophenol, 4-dimethylaminoazobenzene, 2,5-dinitrophenol, 1-Naphthyl Red, Chlorophenol Red, Hematoxylin, 4-nitrophenol, nitrazine yellow, and 3-nitrophenol.

Alternatively, thermochromic dyes may be used that are sensitive to temperature changes in the absorbent article and exhibit a color changing effect, brought on by different temperatures from aqueous medium deposited in the article. Such a temperature change may be brought on by the soiling of the article with urine, menses or bowel movements. Thermochromic dyes or coloring materials for use in the composition include polymers such as polythiophene, and thermochromic liquid crystalline materials. Such dyes/coloring agent materials are available from numerous sources including the H.W. Sands Corporation.

Alternatively, polarity-sensitive dyes for color changing effect may be utilized in the composition. Examples of polarity-sensitive dyes include REICHARDT dye, 1-ethyl-4-methoxycarbonylpridinium Iodide, 2,6-diphenyl-4-(2,4,6-triphenylpyridinium)phenolate (1), 4[(1-methyl-4-(1H)-pyridinylidene)-ethylidene]-2,5-cyclohexadien-1-one (2), and 4-[4-(dimethylamino)styryl]-1-methylpyridinium iodide.

The color changing dyes, desirably pH change dyes, can be present in the composition from about 0.01 wt. % to about 10 wt. %. Typically the amount of pH change dye can be between about 0.05 or 0.1 wt. % to about 4 or 5 wt. %, or 6 or 7 wt. %; desirably the range is between about 0.5 or 1 wt. % to about 2.5, 3 or 5 wt. %, inclusive. If present, the amount of thermochromic dyes or polarity-sensitive dye present in the composition would be similar to the amounts contemplated for leuco or pH dyes.

As previously noted with olfactory indicators, one or more multisensory compositions having different visual indicators can be placed at different locations within the absorbent article. Each may be placed different distances from a peripheral side edge of the absorbent article or layer within the absorbent article.

Depending on the type of dye that is employed in the aqueous medium-sensitive, multisensory indicator coating composition, various other chemistries may be utilized in the composition. For example, as noted for compositions with leuco dyes, it is desirable to include developers. Surfactants and binders are also desirable composition components. Examples of suitable developers include bisphenol A, zinc chloride, zinc salicylate, and phenol resins. Other examples of color developing materials to be used conjointly with the leuco dyes may include: 4-tert-butylphenol, α-naphthol, β-naphthol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'-cyclohexylidene diphenol, 4,4-dihydroxy diphenylsulfide, 4,4'-thiobis(6-tert-butyl-3-methylphenol), 4,4'-dihydroxydiphenyl sulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, novolak type phenol resins, phenol polymers and like phenol compounds. If present, the amount of color developers in the multisensory indicator composition is from about 1 to 25 weight. %, alternatively from about 1 to about 10 weight %. Like the leuco dyes, the color developers generally exhibit good solubility in organic solvents.

If pH change indicator color changing dyes are used as the basis of a visual color changing wetness indicator in the multisensory indicator composition, such composition desirably includes a pH adjuster such that pH is maintained at a certain level prior to exposure to aqueous-based bodily fluids. Upon exposure to such soiling by bodily fluids, the pH of the substrate with coating will change, thereby triggering the color changing effect. The pH adjuster is any molecule or composition that may be used to control the pH of the color changing composition. The pH adjuster may be an acid, a base or a combination of both such as would be found with a buffering composition. The pH adjuster is selected in conjunction with the choice of colorant to be used in the color changing composition. For example, if the color changing composition includes a colorant that has a color transition point that occurs at a pH of lower than 5.5, the selected pH adjuster is desirably an acid to make the pH of the color-changing composition acidic. If the color-changing composition includes a colorant that transitions color at a pH higher than 9.5, the selected pH adjuster is desirably a base to make the pH of the color-changing composition basic.

Examples of suitable acid pH adjusters include organic acids, inorganic acids and polymeric acids; more specifically, examples of such acids include organic acids include glycolic acid, citric acid, lactic acid, ascorbic acid, oxalic acid, maleic acid, tartaric acid, salicylic acid, palmitic acid and stearic acid. Further examples organic acids include polyacrylic acids, polymethacrylic acids and copolymers containing acrylic acids, methacrylic acids or both acrylic acids and methacrylic acids. Examples of suitable basic pH adjusters include organic bases, inorganic bases and polymeric bases; more specifically, examples include sodium hydroxide, sodium carbonate, sodium bicarbonate, sodium borate, potassium hydroxide, polymeric amines, dendrimeric amine and 1,3-pentanediamine.

The pH adjusters are desirably present between about 1 and 30 weight % of the composition, alternatively between about 5 and 20 weight %. Further examples of pH adjusters may be found in US 2011/0015599 to Song et al. which is incorporated herein in its entirety by reference thereto.

The homogeneous coating composition solution may contain a binder so that the solution may be used as an ink suitable for printing and that can be air-dried without heating. Binders specifically serve to make the aqueous medium-sensitive, multisensory indicator composition more suitable for printing. Binders also serve to protect the dye molecules responsible for the color changing effect and the betaine ester molecules responsible for the olfactory change, from environmental moisture experienced as humidity. Additionally, binders create stronger adhesion between the composition molecules and the support or substrate onto which the multisensory indicator composition will be disposed. Suitable binders include, but are not limited to compositions that consist of mainly organic soluble polymeric resins such as modified celluloses, polyesters and polyamides. Organic solvent-based varnishes are also suitable binding compositions. Specific desirable binders include nitrocellulose, cellulose acetate propionate, cellulose acetate butyrate and other non-water soluble binders. Other binders include hydroxyethyl cellulose; methyl cellulose; ethyl cellulose; carboxymethyl cellulose; polymers soluble in an organic solvent such as polyvinylbutyral, polyvinyl acetate, vinyl chloride-vinyl acetate copolymer, acrylic resin, styrene resin, and polyester resin. The binders can be present from about 10, 20, 30 or 70 weight %.

Based on the substrate or surface on which the multisensory, aqueous medium-sensitive indicator composition is to be deposited, the indicator composition may require addition of other ingredients to immobilize or make the dye (color agent), or other components adhere more securely to the substrate. The multisensory indicator composition may therefore also contain wettability enhancing agents such as surfactants and/or water-miscible or hydrophilic polymers. Furthermore, the composition may also contain other additives to adjust viscosity, surface tension, or other physical and chemical properties. Alternatively, the substrates can be treated with different materials to modify their surface properties before the deposition of the multisensory indicator composition, to improve the adhesion of the composition. The wettability enhancing agent can be a single surfactant or a mixture of surfactants. The surfactants can be non-ionic, neutral surfactants, or ionic surfactants. The ionic surfactants can be either positively charged or negatively charged. Examples of non-ionic surfactants include alkyl poly(ethylene oxide) such as copolymers of poly(ethylene oxide) and polypropylene oxide) (commercially called Poloxamers or Poloxamines), alkyl polyglucosides such as octyl glucoside and decyl maltoside, fatty alcohols such as cetyl alcohol, oleyl alcohol, cocamide MEA and cocamide DEA. Examples of ionic surfactants include anionic (e.g., based on sulfate, sulfonate or carboxylate anions) surfactants such as s (SDS), ammonium lauryl sulfate and other alkyl sulfate salts, Sodium laureth sulfate, also known as sodium lauryl ether sulfate (SLES), Alkyl benzene sulfonate, soaps, or fatty acid salts; and cationic (e.g., based on quaternary ammonium cations) surfactants such as Cetyl trimethylammonium bromide (CTAB) a.k.a. hexadecyl trimethyl ammonium bromide, and other alkyltrimethylammonium salts, Cetylpyridinium chloride (CPC), Polyethoxylated tallow amine (POEA), Benzalkonium chloride (BAC), Benzethonium chloride (BZT); or Zwitterionic (amphoteric) surfactants such as Dodecyl betaine, Dodecyl dimethylamine oxide, Cocamidopropyl betaine, Coco ampho glycinate. Alternatively, the wettability enhancing agents may also be hydrophilic molecules. The hydrophilic molecules may also be polymers such as polyethylene glycol and its copolymers. Desirable surfactants include different classes depending on the type of indicator system. For example, for color appearing inks, no surfactant is desirable. For color disappearing inks, nonionic or neutral surfactants are desirable. For pH indicator dye-based inks, charged surfactants are desirable, such as cationic surfactants. Desirably, if such surfactants are present in the composition, they are present in an amount of between about 0.1 to 10 weight %. Alternatively, such surfactants are present in the composition in an amount of between about 0.5 to 10 weight %. Alternatively, such surfactants are present in an amount of between about 1 and 5 weight % of the composition. In one embodiment for pH indicator dye-based ink compositions, such surfactants are desirably present in an amount between 0.1 and 10 weight %, alternatively between 0.5 and 5 weight %.

Additional coating components that may be employed in the composition include desensitizers, especially for use with leuco dyes. Desirably, if used, the desensitizer of the present disclosure is of low molecular weight. Most desirably, the desensitizer is a zwitterionic molecule having a molecular weight of about 100 to about 800, and high solubility in water and organic solvents. One such desensitizer is a betaine. It may also be desirable to use a zwitterionic molecule having a molecular weight of about 100 to about 500; or in the alternative, about 200 to about 400. Suitable types of betaine include poly sugar betaine C, betaine ester-menthol and betaine hydrochloride. Contemplated zwitterionic molecules include 2-(methacryloyloxy) ethyl 3-sulfopropyl) ammonium hydroxide. If present, the amount of desensitizers are desirably present from about 1 weight % to about 30 weight %, alternatively from about 1 weight % to about 15 weight %. Still in a further alternative embodiment, such desensitizers are desirably present from about 1 weight % to about 25 weight %. Still in a further alternative embodiment, such desensitizers are desirably present from about 1 weight % to about 5 weight %. Still in a further alternative embodiment, such desensitizers are desirably present from about 5 weight % to about 10 weight %, alternatively from between about 5 and 15 weight %, alternatively from between about 5 and 25 weight %.

The aqueous medium triggered coating composition of the invention may be applied to an absorbent article, or layer within an absorbent article, by any number of known applications or printing techniques. For example, the coating composition of the present invention may be deposited on a substrate by various surface deposition or printing methods such as flexographic printing, gravure roll printing, stamping, screen print, spraying techniques, dip and squeeze, and digital print methods. Further, the composition may be applied in a melt form and allowed to solidify on a treated substrate.

Placement of the multisensory, aqueous medium-sensitive coatings can be on any number of substrates. The substrate sheets can for instance, include nonwoven or woven sheets. Such sheets can include synthetic or natural fibrous materials and combinations thereof, such as for example, extruded spunbond, and meltblown webs, bonded carded web, or other airlaid materials, spun cellulosic, wool or synthetic yarns. Such sheets may further include cellulosic-based dry or wet laid tissue or paper sheets. Additionally, such substrates may include film sheets, laminates of film and fibrous layers, or laminates of multiple fibrous layers. Furthermore, such substrates may include foams, such as open cell or closed foams. Such substrates/sheets may be placed as layers within absorbent articles, or may themselves serve as the absorbent article, such as as a towel, tissue or wipe.

Placement of such multisensory, aqueous medium-sensitive coating composition in an absorbent article may be across the entire article's longitudinal and transverse or lateral (width) dimensions, or layer of an article, or alternatively, may be limited to certain locations within the article, or layer(s) on the article. For example, such chemistry may be placed at a location specifically designed to contact aqueous-based waste, such as a highly probable "soiling area" in an article's or layer's central crotch region. In another example, such coating composition may be placed adjacent an absorbent article's peripheral side edge on one or more layers, to serve as an indicator of imminent leakage of waste from an absorbent article. For example, in one embodiment, such coating composition is affixed to the absorbent article or at least one layer in the absorbent article, along a longitudinally directed side peripheral edge of the article, or layer respectively. Desirably, such coating chemistry is placed adjacent either the peripheral side edge of the absorbent article, or adjacent a peripheral side edge of the layer within an absorbent article, as a capacity indicator. Such coatings and coated layers may be used in any number of locations and components within the end product (absorbent article) that can come in contact with aqueous medium, including but not limited to the topsheet layer, backsheet layer (inner surface) or absorbent core layer. The coatings may be positioned in numerous separated locations on an individual layer, or on multiple layers, such as in a central insult deposition zone, or along layer/article peripheral edges. Other interior positioned layers may also be coated with the coating composition. In an alternative embodiment, if a relatively hydrophobic betaine ester is selected for the composition (or one having relatively hydrophobic R3-R5 groups), it may be desirable to limit the placement of the coating formulation to certain locations on an absorbent article that would not directly impact the absorbency pathways of an article, such as on an inside surface of a backsheet layer (as opposed to a topsheet layer or absorbent core layer), or side areas of a topsheet layer, absorbent core layer or other interior situated layer.

When a fragrance is detected by a caregiver or user of the absorbent article, even though a visual inspection may not be immediately possible, the caregiver or user would recognize (by the fragrant smell) that wetness has been deposited either at a location adjacent an article's or layer's peripheral side edge within the article, or has spread to a location adjacent the article's or layer's peripheral side edge within the article.

For the purpose of this application, the term "peripheral edge" shall mean an outermost edge of a layer or article. For the purposes of this application, the term "adjacent" shall mean in one embodiment, between about 0 and 5 cm from a peripheral side edge of an absorbent article, or layer within an absorbent article, alternatively between about 0.1 cm and 5 cm from a peripheral side edge. In a further alternative embodiment, the term adjacent shall mean between about 0 and 3 cm from a peripheral side edge of an absorbent article or layer within an absorbent article, alternatively between about 0.1 cm and 3 cm from a peripheral side edge. In still a further alternative embodiment, the term adjacent shall mean between about 0 and 2 cm from a peripheral side edge of an absorbent article or layer within an absorbent article, alternatively, between about 0.1 cm and 2 cm from a peripheral side edge. The article or layer peripheral side edge may be either a longitudinally directed side edge or a front or back end side edge. It should be appreciated that the placement of the coating on the absorbent article or layer within the absorbent article can be in one embodiment, adjacent any peripheral side edge of the article or layer within the article in order to serve as a desirable capacity indicator. Alternatively, such coating can be placed only along article or layer peripheral side edges (at discrete localized spots) that have propensities to leak, such as the wing or flap areas (as in the case of feminine care absorbent articles), or the leg openings, crotch side areas, or waist opening areas (as in the case of diaper and incontinence-style products). Alternatively, such coating composition can be placed in locations not adjacent a peripheral side edge of the article or layer within an article, so as to provide an immediate indication of soiling (by release of fragrance) and odor masking feature. This may be especially beneficial for a product application in which a consumer has an extreme propensity for irritation on prolonged exposure to liquid moisture, or for a consumer that is particularly interested in maintaining discretion and assurance of their absorbent products not leaking and causing stains. The coating with color changing dye and betaine ester can be applied as either a monochromatic color scheme, bichromic, or in multiple colors, or printed/applied in various shapes and sizes, graphics of patterns or alpha numeric symbols and/or words (such as trademarks or messages), or combinations thereof. Therefore, the release of the fragrant volatile may be used to mask an offensive odor, an aromatic cue that soiling has occurred or that article capacity has been reached or is about to be reached (and that leakage may be imminent).

In an alternative embodiment, the indicator coating of the present invention can be applied/affixed at multiple separate locations along the article dimensions, each with either different olfactory indicators or visual indicators in the composition, such that different smells or different changes in color released to, or viewed by the consumer, would present a graduated warning system of imminent leakage, each smell or color indicating a different distance from the article or layer peripheral side edge. By providing both a graduated visual and aromatic cue to a consumer or caregiver, avoidance of a leak from an absorbent article may be avoided. It is desirable in one embodiment, that such multisensory, aqueous medium triggered coating composition be initially in the form of a homogeneous liquid (solution), an emulsion, an ink, a suspension or hot meltable solid and then deposited on a solid substrate, such as for example a film, nonwoven or woven sheet, or aqueous absorbent core layer sheet material.

In one desirable embodiment of the multisensory, aqueous medium-sensitive coating composition of the invention, the coating composition includes a betaine ester or betaine ester derivative with functional active, and at least one additional aqueous medium triggerable indicator, for providing a visual indication of an aqueous liquid with such visual indicator being a color changing pH indicator dye with a pH adjuster. In still a further embodiment of the coating composition, the composition may include a betaine ester or betaine ester derivative with functional active, a color changing pH indicator dye, a pH adjuster such as an acid or base, a surfactant, and a binder. Additionally, as previously noted, the coating composition desirably includes a solvent.

In still a further alternative embodiment of the invention, such coated polymeric film, woven or nonwoven sheets or laminates thereof, are utilized in at least one component/part of a disposable absorbent article. Such coated material may be for example, used as a coated backsheet, topsheet or absorbent core layer component of a disposable absorbent article. In still a further alternative embodiment, such coated material may be employed as a component of a wipe or cleaning absorbent sheet. By using such coated materials in an absorbent article, such composition can be used to detect wetness in an aqueous medium, or soiling of an article from urine, vaginal secretions, mucous, menses, feces or a household spill. Further, such composition can at the same time also mask odors and provide aesthetic features to an absorbent article. Formulations of the above coatings are demonstrated through the following series of examples.

EXAMPLES

The following components were blended together to form multisensory, wetness indicating coating compositions for the purpose of demonstrating the effectiveness of using a betaine ester and dye/ink according to the present disclosure.

Example 1 (without Betaine Ester Functional Active)

A butanone solution was prepared which contained 20% acetate butyratecellulose (binder), 1% crystal violet lactone (leuco dye), 12% zinc salicylate (developer), 10% Pluronic P 85 of BASF (wettability agent), 5% sodium decadnoic sulfate (surfactant) and 1% eugenol (not betaine ester). The solution was brushed on a polypropylene outer cover film material and air-dried. The eugenol scent was readily detected continuously by a human nose when approaching the film. The eugenol smell was detected by normal inhalation through the human nose (from the same distance) for about four days under ambient conditions. After four days, little eugenol smell was detected by a human nose, even after wetting. A spike of eugenol smell was detected when a freshly prepared film sample (no more than 24 hours old) was wetted by water. At the same time, the film color went from blue to colorless when wetted.

Example 2

A butanone solution was prepared which contained 20% acetate butyratecellulose, 1% crystal violet lactone, 12% zinc salicylate, 10% Pluronic P 85, 5% sodium decadnoic sulfate and 1% eugenol betaine ester. The solution was brushed on a polypropylene outer cover film and air-dried. No smell of eugenol was detected by human nose when approaching the film. When wetted, eugenol smell was readily detected by a human nose. The sample was allowed to remain under ambient conditions for two months; eugenol smell was readily detected by a human nose upon being wetted by water. At the same time, the film color went from blue to colorless after being wetted.

Example 3 (Example Using Color Changing pH Indicator Dye)

A solution was made by dissolving 10 mg bromocresol green (pH dye), 100 mg citric acid (pH adjuster), 50 mg polyacrylic acid (pH adjuster), 30 mg benzethenium chloride (wettability enhancing agent) and 300 ml nitrocellulose-based varnish (binder) from Sunchemical Co. in 500 microliters ethanol. 20 mg betaine ester of menthol dissolved in 100 microliters ethanol was added to the solution and mixed well. The solution was brushed on a piece of polypropylene film to form a thin coating and air-dried overnight. Smell of menthol was detected when the coating was wetted with water. The color of the coating changes from yellow to blue.

A wetness indicator containing the multisensory coating composition for detecting the presence of an aqueous-based liquid that has penetrated the absorbent article, is desirably immobilized or printed on one or more layers of an absorbent article. Such wetness indicator coating composition can be positioned for example on the topsheet layer. In such a situation, the wetness indicator can be positioned on a user facing surface of the topsheet layer, a garment facing surface of the topsheet layer, or impregnated or within the topsheet layer itself. In an alternative embodiment, the wetness indicator coating composition can be positioned along the longitudinally directed side edges of the topsheet layer so as to not only provide a visual and aromatic indication of soiling of the article, but also to serve as a warning system to warn a user or caregiver of impending leakage of the article as aqueous medium seeps to the longitudinally directed side edges of such an article. In a further alternative embodiment, the wetness indicator may be positioned in discrete zones on the topsheet layer, or alternatively across the entire surface of the topsheet layer. In another embodiment, the wetness indicator can be positioned along the inside user facing surface of the backsheet layer. As with the previously described topsheet layer, such an indicator may be positioned in discrete zones or across the entire inside, user facing surface of the backsheet layer. Still in a further alternative embodiment, the wetness indicator may be positioned on either exterior surface of the absorbent core layer (either the user facing surface or the garment facing surface), or within the absorbent core layer or layers, if such absorbent core includes multiple layers. In any event, it is desirable for the wetness indicating coating composition be visible to either the caregiver or the user. For example, by positioning such a composition on the inside, user-facing surface of a backsheet layer, the indicating composition is desirably visible to a caregiver through the garment facing surface of the backsheet layer of the article. By positioning the coating composition along the side edges of an article, similarly, such composition is desirably visible to a user of such articles as feminine care pads and liners.

Generally speaking, the multisensory, aqueous medium triggered coating composition of the present disclosure can be incorporated into an absorbent article in a variety of different orientations and configurations, so long as the coating composition is capable of receiving aqueous bodily fluids or waste (e.g., urine and/or fecal material) and providing a signal to a user or caregiver regarding the presence or absence of the aqueous liquid. For instance the indicating coating composition can directly be immobilized or printed on a portion of the inner side of a backsheet film layer, a top user-facing side of the topsheet layer, an inner surface of the topsheet layer, or any internal layer surface in communication with liquid, of the article. The coating composition may also be or printed or immobilized on a piece of substrate to make a wetness indicator of different patterns which is sandwiched between the outer cover film and the absorbent core layer of the article, or between other layers of an absorbent article.

The coating composition can be visible to the user or caregiver so that a simple, accurate, and rapid indication of wetness can be provided. The visibility can be accomplished in a variety of ways. For example, in some embodiments, the absorbent article can include a transparent or transluscent portion (e.g., window, film, etc.) that allows the coating composition to be readily viewed without removal of the absorbent article from the wearer and/or without disassembly of the absorbent article. In other embodiments, the coating composition can extend through a hole or aperture in the absorbent article for observation. In still other embodiments, the coating composition can simply be positioned on a surface of the absorbent article for observation. Regardless of the particular manner in which it is integrated, urine or other aqueous liquid can be directly discharged to a portion of the coating composition, or can be discharged onto a component of the absorbent article into which the coating composition has been integrated.

The wetness indicating coating composition on the article desirably shows a strong color in its dry state. The strong color of the indicating coating composition material desirably changes to a second color when in contact with water or aqueous medium. Alternatively, the color becomes week or disappears completely. The aqueous medium can be, for example, bodily fluids or waste, such as mucous, menses, vaginal secretions, urine, feces or household spills.

Reference now will be made in detail to various absorbent article embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment.

In particular, a rear perspective view of a baby care diaper 120 is illustrated in FIG. 1. The diaper 120, may or may not be disposable. A diaper chassis, as illustrated, can have an hourglass shape in an unfastened configuration. However, other shapes can of course be utilized, such as a generally rectangular shape, a T-shape, or an I-shape. The diaper may include a chassis formed by various components, including an outer cover or backsheet layer, a bodyside liner or topsheet layer, at least one aqueous liquid, absorbent core layer, and an optional surge layer. It should be understood, however, that other layers can also be used in exemplary embodiments of the present disclosure. Likewise, one or more of the layers can also be eliminated in certain exemplary embodiments of the present disclosure. By way of illustration only, various materials and methods for constructing absorbent articles such as the diaper 120 are disclosed in PCT Patent Application WO 00/37009 to Fletcher et al.; U.S. Pat. No. 4,940,464 to Van Gompel et al.; U.S. Pat. No. 5,766,389 to Brandon et al., and U.S. Pat. No. 6,645,190 to Olson et al. which are incorporated herein in their entirety by reference thereto.

Figure 2:
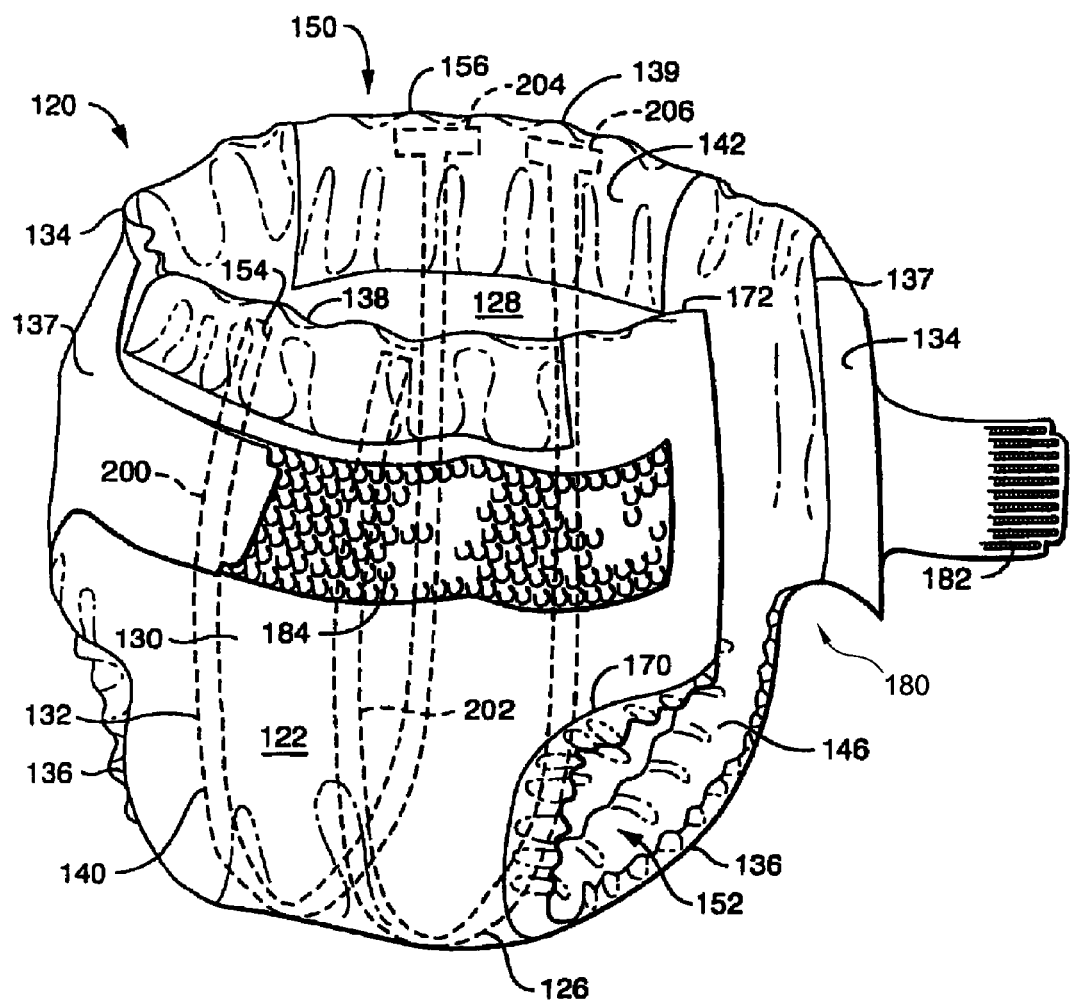
FIG. 2 is a front perspective view of the diaper embodiment illustrated in FIG. 1.
Figure 3:
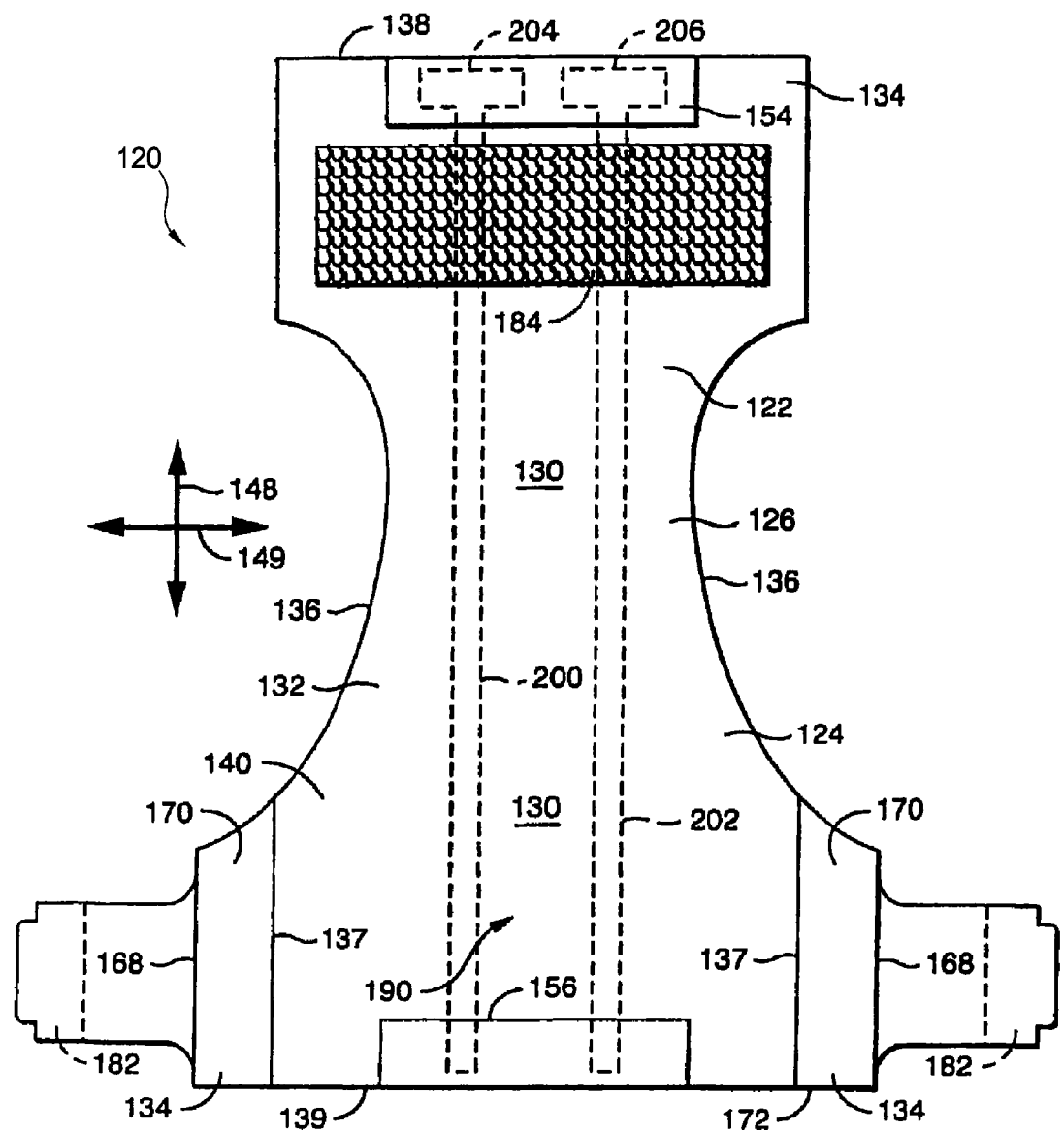
FIG. 3 is a plan view of the diaper embodiment shown in FIG. 1 with the diaper in an unfastened, unfolded and laid flat condition showing the surface of the article that faces away from the wearer (garment facing side).
Figure 4:
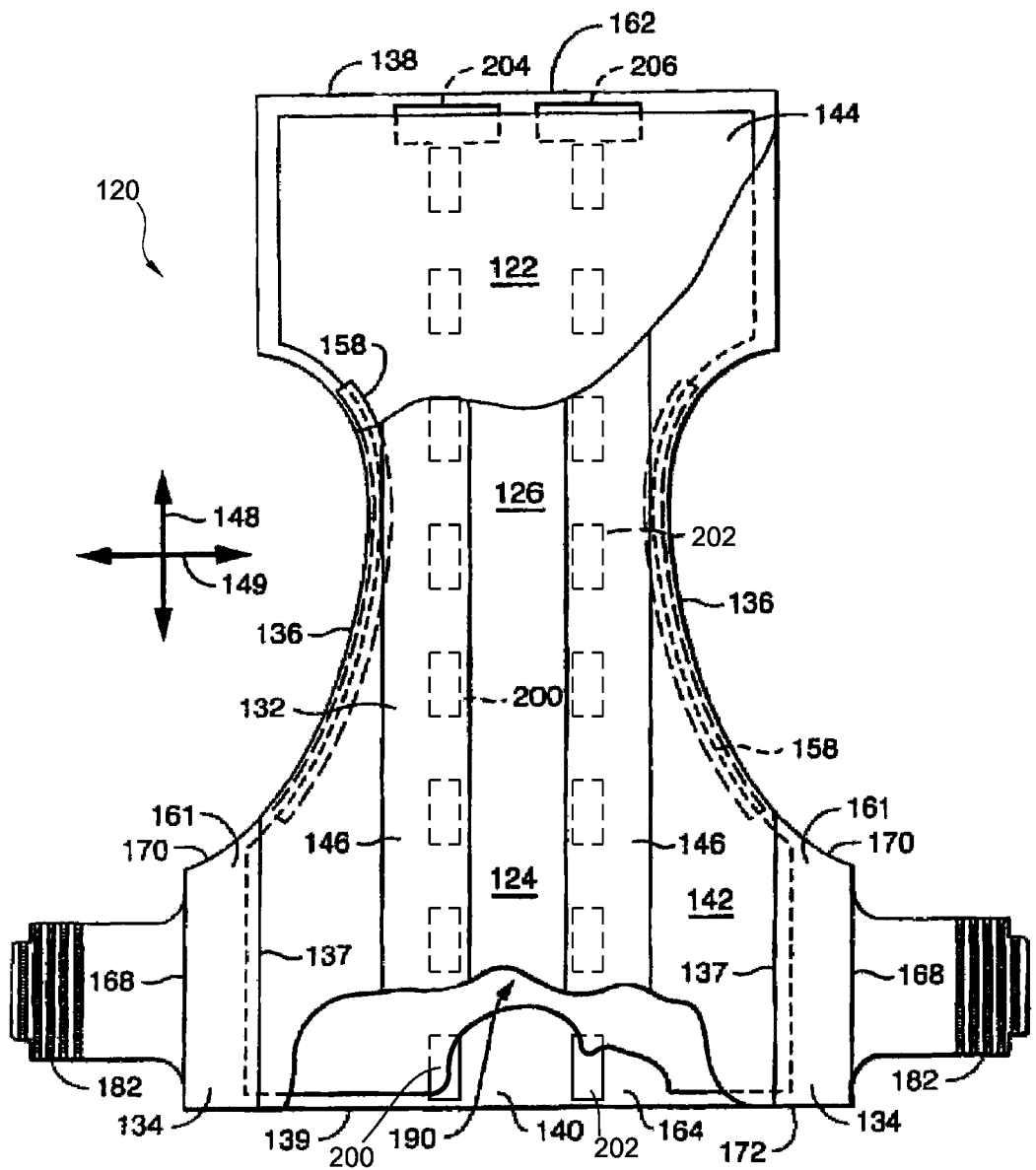
FIG. 4 is a cut-away plan view of an alternative embodiment of the diaper absorbent article shown in FIG. 3, which shows the surface of the article that faces the wearer skin when worn.

The diaper 120 is representatively illustrated in FIG. 1 in a partially fastened condition. The diaper 120 shown in FIGS. 1 and 2 is also represented in FIGS. 3 and 4 in an opened and unfolded state. Specifically, FIG. 3 is a plan view illustrating the exterior side of the diaper 120, while FIG. 4 illustrates an alternative embodiment of the interior side of the diaper 120. As shown in FIGS. 3 and 4, the diaper 120 defines a longitudinal direction 148 that extends from the front of the article when worn to the back of the article. Opposite to the longitudinal direction 148 is a lateral (or transverse) direction 149.

The diaper 120 defines a pair of longitudinal end regions, otherwise referred to herein as a front end region 122 and a back end region 124, and a center region, otherwise referred to herein as a crotch region 126, extending longitudinally between and interconnecting the front end and back end regions 122, 124. The diaper 120 also defines an inner surface 128 adapted in use (e.g., positioned relative to the other components of the article 120) to be disposed toward the wearer, and an outer surface 130 opposite the inner surface. The front and back regions 122, 124 are those portions of the diaper 120, which when worn, wholly or partially cover or encircle the waist or mid-lower torso of the wearer. The crotch region 126 (central liquid deposition zone) generally is that portion of the diaper 120 which, when worn, is positioned between the legs of the wearer and covers the lower torso and crotch of the wearer. The absorbent article 120 has a pair of laterally opposite side edges 136 and a pair of longitudinally opposite waist edges, respectively designated front waist edge 138 and back waist edge 139. The illustrated diaper 120 includes a chassis 132 that, in this aspect, encompasses the front region 122, the back region 124, and the crotch region 126. Referring to FIGS. 3-4, the chassis 132 includes a garment facing backsheet layer 140 and a user facing topsheet layer 142 (FIGS. 1-4) that may be joined to the backsheet layer 140 in a superimposed relation therewith by adhesives, ultrasonic bonds, thermal bonds or other conventional techniques.

Generally, the user facing topsheet layer 142 can be employed to help isolate the wearer's skin from liquids held in the absorbent core layer 144. For example, the topsheet layer 142 presents a bodyfacing surface that is typically compliant, soft feeling, and non-irritating to the wearer's skin. Typically, the topsheet layer 142 is also often less hydrophilic than the absorbent core layer 144 so that its surface remains relatively dry to the wearer. As indicated above, the topsheet layer 142 can be liquid-permeable to permit liquid to readily penetrate through its thickness. Exemplary topsheet layer constructions that contain a nonwoven web are described in U.S. Pat. No. 5,192,606 to Proxmire, et al.; U.S. Pat. No. 5,702,377 to Collier, I V, et al.; U.S. Pat. No. 5,931,823 to Stokes, et al.; U.S. Pat. No. 6,060,638 to Paul, et al.; and U.S. Pat. No. 6,150,002 to Varona, as well as US Patent Application Publication Nos. 2004/0102750 to Jameson; 2005/0054255 to Morman, et al.; and 2005/0059941 to Baldwin, et al., all of which are incorporated herein in their entirety by reference thereto.

The garment facing backsheet layer 140 typically can be formed from a material that is substantially impermeable to liquids. For example, the backsheet layer 140 can be formed from a thin plastic film or other flexible liquid-impermeable material, such as a hydrophobic nonwoven or nonwoven laminate material. In one embodiment, the backsheet layer 140 is formed from a polyolefin (polyethylene) film having a thickness of from about 0.01 millimeter to about 0.05 millimeter. The film can be impermeable to liquids, but permeable to gases and water vapor (i.e., "breathable"). This permits vapors to escape from the absorbent core layer 144, but still prevents liquid exudates from passing through the backsheet layer 140. If a more cloth-like feeling is desired, the backsheet layer 140 can be formed from a polyolefin film laminated to a nonwoven web. For example, a stretch-thinned filled polyolefinic film can be thermally laminated to a spunbond web of polypropylene fibers.

Referring to FIG. 4, the topsheet layer 142 may suitably be joined to the backsheet layer 140 along the perimeter of the chassis 132 to form a front waist seam 162 and a back waist seam 164. As shown in FIG. 4, the topsheet layer 142 may suitably be joined to the backsheet layer 140 to form a pair of side seams 161 in the front region 122 and the back region 124. The topsheet layer 142 can be generally adapted, i.e., positioned relative to the other components of the article 120, to be disposed toward the wearer's skin during wear of the absorbent article 120.

The chassis 132 may further include an absorbent core layer structure, or aqueous liquid retaining absorbent core layer 144 particularly shown in FIG. 4 disposed between the backsheet layer 140 and the topsheet layer 142 for absorbing liquid body exudates exuded by the wearer. The diaper can also contain a substantially hydrophilic tissue wrapsheet or extruded nonwoven wrapsheet (not shown), that helps maintain the integrity of a fibrous or superabsorbent structure of the absorbent core layer 144. The tissue wrapsheet is typically placed about the absorbent core layer 144 over at least the two major facing surfaces thereof, and is composed of an absorbent cellulosic material, such as creped wadding or a high wet-strength tissue. The tissue or nonwoven wrapsheet can be configured to provide a wicking layer that helps to rapidly distribute liquid over the mass of absorbent fibers of the absorbent core layer 144. The wrapsheet material on one side of the absorbent fibrous mass can be bonded to the wrapsheet located on the opposite side of the fibrous mass to effectively entrap the absorbent core layer 144. Furthermore, the diaper 120 can also include a ventilation layer (not shown) that is positioned between the absorbent core layer 144 and the backsheet layer 140. When utilized, the ventilation layer can help insulate the backsheet layer 140 from the absorbent core layer 144, thereby reducing dampness in the backsheet layer 140. Examples of such ventilation layers can include a nonwoven web laminated to a breathable film, such as described in U.S. Pat. No. 6,663,611 to Blaney, et al., which is incorporated herein in its entirety by reference thereto.

The diaper can also include a pair of containment flaps 146 that are configured to provide a barrier and to contain the lateral flow of body exudates. The containment flaps 146 can be located along the laterally opposed side edges of the topsheet layer 142 adjacent the side edges of the absorbent core layer 144. The containment flaps 146 can extend longitudinally along the entire length of the absorbent core layer 144, or can only extend partially along the length of the absorbent core layer 144. When the containment flaps 146 are shorter in length than the absorbent core layer 144, they can be selectively positioned anywhere along the side edges of diaper 120 in a crotch region. In one embodiment, the containment flaps 146 extend along the entire length of the absorbent core layer 144 to better contain the body exudates. Such containment flaps 146 are generally well known to those skilled in the art. For example, suitable constructions and arrangements for the containment flaps 146 are described in U.S. Pat. No. 4,704,116 to Enloe, which is incorporated herein in its entirety by reference thereto. An illustrated, a pair of containment flaps 146 is shown secured to the topsheet layer 142 for inhibiting the lateral flow of body exudates. The elasticized containment flaps 146 as shown in FIG. 4 define a partially unattached edge which assumes an upright configuration in at least the crotch region 126 of the diaper 120 to form a seal against the wearer's body when in use. As shown, the containment flaps 146 extend longitudinally along the entire length of the chassis 132.

To further enhance containment and/or absorption of body exudates, the diaper 120 may also suitably include leg elastic members 158 (FIG. 4), as are known to those skilled in the art. The leg elastic members 158 can be operatively joined to the backsheet layer 140 and/or the topsheet layer 142 and positioned in the crotch region 126 of the absorbent article 120. The leg elastic members 158 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 158 may include a plurality of dry-spun coalesced multifilament spandex elastomeric threads sold under the trade name LYCRA.

In some aspects, the absorbent article 120 may further include a surge management layer (not shown) which may be optionally located adjacent the absorbent core layer structure 144 and attached to various components in the article 120 such as the absorbent core layer structure 144 or the bodyside liner 142 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into storage or retention portions of the absorbent core layer 144 structure. Examples of suitable surge management layers are described in U.S. Pat. No. 5,486,166 to Bishop et al. and U.S. Pat. No. 5,490,846, to Ellis et al. Other suitable surge management materials are described in U.S. Pat. No. 5,820,973, to Dodge III et al. The entire disclosures of these patents are hereby incorporated by reference herein.

As shown in FIGS. 1-4, the absorbent article 120 further includes a pair of opposing elastic side panels 134 that are attached to the back region of the chassis 132. As shown particularly in FIGS. 1 and 2, the side panels 134 may be stretched around the waist and/or hips of a wearer in order to secure the garment in place. As shown in FIGS. 1 and 2, the elastic side panels (or ears) are attached to the chassis along a pair of opposing longitudinal edges 137. The side panels 134 may be attached or bonded to the chassis 132 using any suitable bonding technique. For instance, the side panels 134 may be joined to the chassis by adhesives, ultrasonic bonds, thermal bonds, or other conventional techniques. In an alternative aspect, the elastic side panels may also be integrally formed with the chassis 132. For instance, the side panels 134 may include an extension of the topsheet layer 142, of the backsheet layer 140, or of both the topsheet layer 142 and the backsheet layer 140. In the aspects shown in the figures, the side panels 134 are connected to the back region of the absorbent article 120 and extend over the front region of the article when securing the article in place on a user. It should be understood, however, that the side panels 134 may alternatively be connected to the front region of the article 120 and extend over the back region when the article is donned.

With the absorbent article 120 in the fastened position as partially illustrated in FIGS. 1 and 2, the elastic side panels 134 may be connected by a fastening system 180 to define a 3-dimensional diaper configuration having a waist opening 150 and a pair of leg openings 152. The waist opening 150 of the article 120 is defined by the waist edges 138 and 139 which encircle the waist of the wearer.

In the aspects shown in the figures, the side panels are releasably attachable to the front region 122 of the article 120 by the fastening system. It should be understood, however, that in other aspects the side panels 134 may be permanently joined to the chassis 132 at each end. The side panels 134 may be permanently bonded together, for instance, when forming a training pant.

The elastic side panels 134 each have a longitudinal outer edge 168, a leg end edge 170 disposed toward the longitudinal center of the diaper 120, and waist end edges 172 disposed toward a longitudinal end of the absorbent article. The leg end edges 170 of the absorbent article 120 may be suitably curved and/or angled relative to the lateral direction 149 to provide a better fit around the wearer's legs. However, it is understood that only one of the leg end edges 170 may be curved or angled, such as the leg end edge of the back region 124, or alternatively, neither of the leg end edges may be curved or angled, without departing from the scope of the present disclosure. As shown in FIG. 4, the outer edges 168 are generally parallel to the longitudinal direction 148 while the waist end edges 172 are generally parallel to the transverse axis 149. It should be understood, however, that in other aspects the outer edges 168 and/or the waist edges 172 may be slanted or curved as desired. Ultimately, the side panels 134 are generally aligned with a waist region 190 of the chassis.

The fastening system 180 may include laterally opposite first fastening components 182 adapted for refastenable engagement to corresponding second fastening components 184. In the aspect shown in the figures, the first fastening component 182 is located on the elastic side panels 134, while the second fastening component 184 is located on the front region 122 of the chassis 132. In one aspect, a front or outer surface of each of the fastening components 182, 184 includes a plurality of mating or complimentary engaging elements. The engaging elements of the first fastening components 182 are adapted to repeatedly engage and disengage corresponding engaging elements of the second fastening components 184 to releasably secure the article 120 in its three-dimensional configuration.

The fastening components 182, 184 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 182 include hook fasteners and the second fastening components 184 include complementary loop fasteners. Alternatively, the first fastening components 182 may include loop fasteners and the second fastening components 184 may be complementary hook fasteners. In another aspect, the fastening components 182, 184 can be interlocking similar surface fasteners, or adhesive and cohesive fastening elements such as an adhesive fastener and an adhesive-receptive landing zone or material, or the like. Further such fastening components 182 may be combination of hook and loop elements, and adhesives elements. One skilled in the art will recognize that the shape, density and polymer composition of the hooks and loops may be selected to obtain the desired level of engagement between the fastening components 182, 184. Suitable fastening systems are also disclosed in the previously incorporated PCT Patent Application WO 00/37009 to Fletcher et al. and the previously incorporated U.S. Pat. No. 6,645,190 to Olson et al.

In the aspect shown in the figures, the fastening components 182 are attached to the side panels 134 along the edges 168. In this aspect, the fastening components 182 are not elastic or extendable. In other aspects, however, the fastening components may be integral with the side panels 134. For example, the fastening components may be directly attached to the side panels 134 on a surface thereof.

In addition to possibly having elastic side panels, the absorbent article 120 may include various waist elastic members for providing elasticity around the waist opening. For example, as shown in the figures, the absorbent article 120 can include a front waist elastic member 154 and/or a back waist elastic member 156.

The various regions and/or components of the diaper 120 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the backsheet layer 140 and topsheet layer 142 are assembled to each other and the absorbent core layer 144 using an adhesive. Alternatively, the absorbent core layer 144 can be connected to the backsheet layer 140 using conventional fasteners, such as buttons, hook and loop type fasteners, adhesive tape fasteners, and so forth. Similarly, other diaper components, such as the leg elastic members, waist elastic members and fasteners, can also be assembled into the diaper 120 using any attachment mechanism.

As seen in FIGS. 1-3, multisensory wetness indicators of the inventive coating compositions 200, 202 are affixed on the diaper 120 inside surface (user facing surface) of the backsheet layer 140, between the absorbent core layer 144 and the backsheet layer 140, along the central crotch region longitudinal direction 148 of the article. Such longitudinally directed stripes of the coating composition terminate in horizontal (laterally directed) portions 204 and 206 such that if the absorbent article is being worn, such wetness indicator can be seen in the waist area of the worn diaper, while such diaper is being worn, and assuming that such soiling has spread to the waist area. Further, if the product is soiled, such indicator will be visually seen along multiple directions. As can be seen in FIG. 4, which illustrates an alternative embodiment of the diaper of FIG. 1, such wetness indicators 200, 202 may alternatively consist of discontinuous dashes rather than continuous lines running from the front end to the back end of the diaper 120. In still a further alternative embodiment, such indicators may be affixed to the inside surface of the backsheet layer, adjacent the peripheral longitudinally directed side edges near the leg openings, or adjacent the peripheral lateral side edges near the waist opening. In particular, such indicators may be affixed adjacent opposite side edges 136 and/or the pair of longitudinally opposite waist edges, respectively designated by 138 and 139. In such an instance, if wetness is deposited in these areas, or migrates to these areas, a scent will be released indicating imminent leakage. It should be recognized, that with respect to the diaper 120 embodiment illustrated in FIGS. 1-4, such coating composition may alternatively be positioned adjacent peripheral side edges of one or more of the topsheet layer, the absorbent core layer, or any other interior diaper layer (on either the user facing side surfaces or garment facing side surfaces, or multiple surfaces). The coating composition can also be placed on or within multiple layers.

Figure 5:
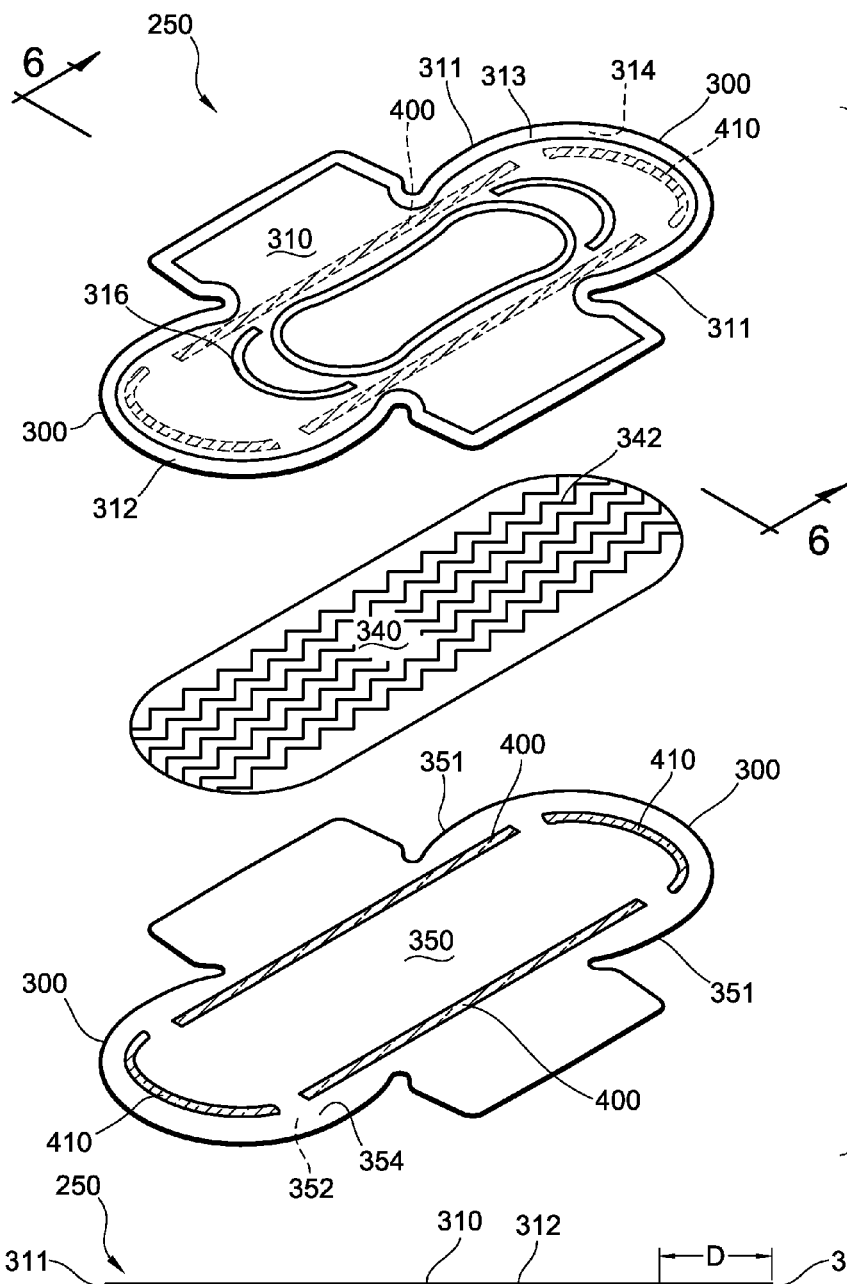
FIG. 5 is an exploded perspective view of an alternative embodiment of an absorbent article of the invention in the form of a feminine hygiene pad, having multisensory wetness indicators shown in various article locations adjacent the article's peripheral side edges, and various layer peripheral side edges.
Figure 6:
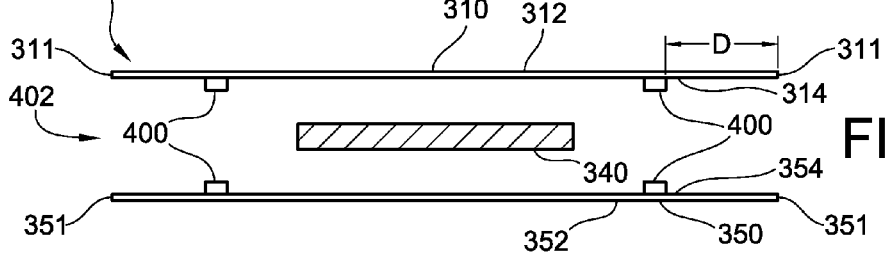
FIG. 6 is an exploded cross-sectional view of the feminine hygiene pad of FIG. 5 taken along line 6-6.

As can be seen in FIGS. 5 and 6, which illustrate an alternative embodiment of an absorbent article with multi-sensory wetness indicators including the composition of the invention, a feminine care pad 250 is illustrated. As can be seen in the exploded perspective view of FIG. 5, the feminine care pad 250 includes a topsheet layer 310 having an embossing pattern in the shapes of arcs 316 and a racetrack design, an absorbent core layer 340 having an embossing pattern in the shapes of zigzags or waves 342, and a backsheet layer 350. The topsheet layer 310 includes an upper user-facing surface 312 and a lower garment facing surface 314. A sealing area 313 seals the topsheet layer 310 to the backsheet layer 350. The topsheet layer 310 includes front and back ends 300 having peripheral side edges, and longitudinally directed side peripheral edges 311. The coating composition of the invention is affixed in one embodiment to the inside garment facing surface 314 of the topsheet layer 310 shown in lines 400, adjacent the longitudinally directed side peripheral edges 311 of the topsheet layer 310. Alternatively, such coating composition could just as easily been affixed in similar positions along the user facing surface 312 of the topsheet layer 310. Further inventive coating composition is optionally affixed to the inside garment facing surface of the topsheet layer 314, in arcs 410 adjacent the peripheral front and rear end 300 edges of the topsheet layer 310.

As seen along the backsheet layer 350 of FIG. 5, additional wetness indicators 400, 410 of the inventive composition are optionally also positioned along the inside user facing surface 354 of the backsheet layer 350, adjacent the longitudinally directed backsheet peripheral side edges 351. The backsheet layer 350 includes an inside user facing surface 354 and a garment facing surface 352. For the purposes of a feminine care absorbent article 250, it may be desirable in one embodiment, for the indicator composition to not be visible through the backsheet garment facing surface 352, so as to avoid being seen through a user's undergarment inadvertently. As seen in FIG. 6, in the exploded cross-sectional view of the feminine care pad 250 of FIG. 5, taken along lines 6-6, the wetness indicators having the coating composition of the invention 400 are affixed within the pad 250 adjacent the pad peripheral longitudinal side edges 402. Such inventive coating compositions are positioned adjacent the longitudinally directed side peripheral edges 311, 351, separated from the longitudinally directed side peripheral edges by a distance "D", which is desirably in one embodiment, less than or equal to 5 cm, alternatively between about 0.1 cm and 5 cm.

Figure 7:
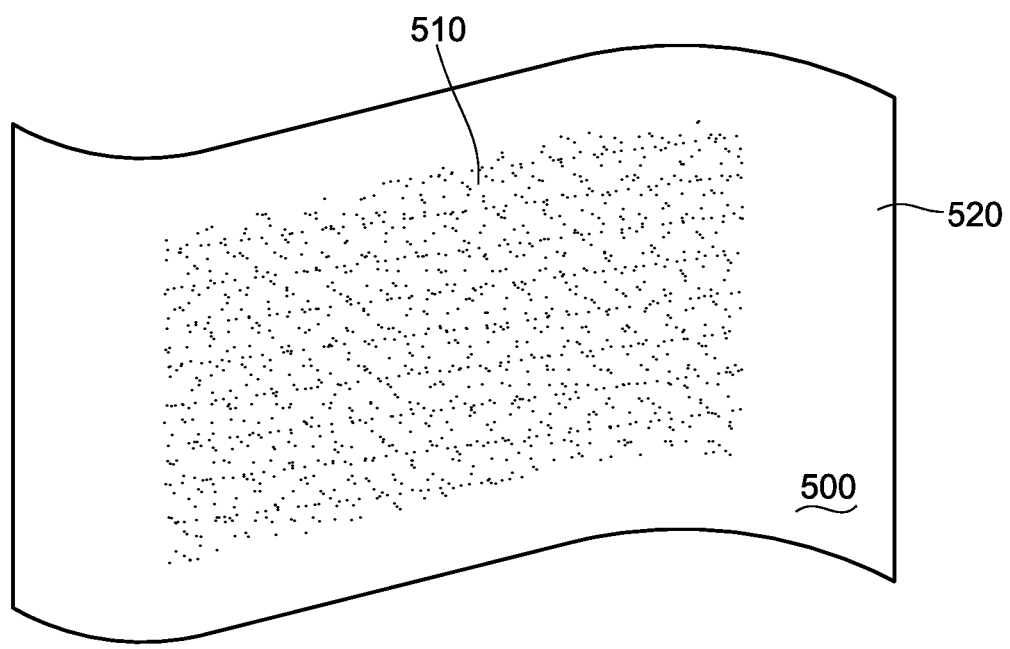
FIG. 7 is a top perspective view of an alternative embodiment of an absorbent article of the invention in the form of an absorbent sheet with the inventive multisensory, aqueous medium sensitive coating applied thereto.

Referring now to FIG. 7, a perspective view of a further absorbent article coated with the coating of the invention is shown. In particular a coated cellulosic-based towel 500 is illustrated having the coating composition 510 printed along the central, liquid absorbing portion of the towel, with uncoated portions 520 along the towel periphery.

The present invention has been described in general and in detail by means of examples. Persons of skill in the art understand that the invention is not limited necessarily to the embodiments specifically disclosed, but that modifications and variations may be made without departing from the scope of the invention as defined by the following claims or their equivalents.

I claim:

1. An aqueous medium-sensitive, coating composition for triggered release of an active ingredient and visual indication of the presence of aqueous medium, comprising:

a betaine ester including a fragrance radical and having a formula

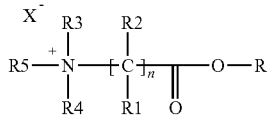

wherein
X⁻ is an anion;
n is an integer between 1 and 4;
R is a radical of a volatile fragrance alcohol with one or more hydroxyl groups; and
R1, R2, R3, R4, and R5 are each independently selected from the group consisting of hydrogen, alkyl, hydroxyalkyl, aryl or aromatic groups;
wherein said active ingredient is the fragrance radical on the betaine ester; and
a visual, color changing wetness indicator, which changes color from a first color to a second color upon a change of condition, wherein said visual, color changing wetness indicator includes at least one of a pH indicator dye and pH adjuster, a thermochromic dye, and a polarity-sensitive dye.

2. The aqueous medium-sensitive coating composition of claim 1, wherein said visual, color changing wetness indicator comprises at least a pH indicator dye and a pH adjuster.

3. The aqueous medium-sensitive coating composition of claim 1, wherein said fragrance radical is derived from the group of fragrances selected from thymol, vanillin, menthol and eugenol.

4. The aqueous medium-sensitive coating composition of claim 1 wherein said composition includes at least a pH indicator dye, a pH adjuster, a surfactant, and a binder.

5. The aqueous medium-sensitive coating composition of claim 1 applied to an absorbent article.

6. The aqueous medium-sensitive coating composition of claim 5 wherein said absorbent article includes at least a topsheet layer, backsheet layer and absorbent core layer between said topsheet layer and backsheet layer, and further wherein said coating composition is applied to at least one layer within said absorbent article.

7. The aqueous medium-sensitive coating composition of claim 6, wherein each of said layers include at least one peripheral side edge and said coating composition is applied adjacent said peripheral side edge of at least one layer.

8. The aqueous medium-sensitive coating composition of claim 5, wherein said article is selected from the group consisting of feminine care articles, baby and child care articles, adult incontinence articles, and absorbent sheet cleaning articles.

9. The aqueous medium-sensitive coating composition of claim 5, wherein said absorbent article includes at least one peripheral side edge, and said coating composition is located adjacent said at least one peripheral side edge.

10. An absorbent article comprising at least a single absorbent core layer, wherein said absorbent core layer includes the coating composition of claim 1.

11. The absorbent article of claim 10 wherein said absorbent core layer includes a peripheral side edge and said coating composition is applied to said absorbent core layer at least adjacent said peripheral side edge.

12. An absorbent article, comprising at least a topsheet layer, a backsheet layer and an absorbent core layer each having central insult deposition zone and at least one peripheral side edge, wherein said coating composition of claim 1 is applied to at least one of said topsheet layer, backsheet layer and absorbent core layer in either said central insult deposition zone or adjacent said at least one peripheral side edge.

13. The absorbent article of claim 12, wherein said absorbent article includes a peripheral side edge and said coating composition is applied to a portion of said absorbent article adjacent said peripheral side edge.

14. The absorbent article of claim 12, wherein said topsheet layer, backsheet layer and absorbent core layer each include a peripheral side edge, and said coating composition is applied adjacent to at least one peripheral side edge of at least one of said topsheet layer, backsheet layer or absorbent core layer.

15. The absorbent article of claim 14, wherein said coating composition includes a color changing pH indicator dye, and a pH adjuster.

16. The absorbent article of claim 15, wherein said coating composition includes a binder.

17. The absorbent article of claim 12, wherein said absorbent article includes a coating of said coating composition in at least two separate areas of said article.

18. The absorbent article of claim 12, wherein said absorbent article includes longitudinally directed side peripheral edges and front and back end peripheral edges and said coating composition is applied adjacent at least one of said longitudinally directed side peripheral edge and front and back end peripheral edge.

19. The absorbent article of claim 18, wherein said coating composition is applied adjacent each of said longitudinally directed side peripheral edges and said front and back end peripheral edges.

20. An absorbent article comprising at least one absorbent core layer, wherein said absorbent article including a longitudinally directed side peripheral edge, said absorbent article including an aqueous medium-sensitive coating composition for triggered release of active ingredients from said absorbent article, said aqueous medium-sensitive coating composition being affixed to said absorbent article adjacent said longitudinally directed side peripheral edge, with said coating composition including a betaine ester including a functional active group and having a formula

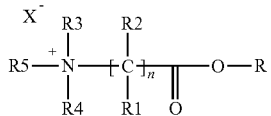

wherein
$X^-$ is an anion;
n is an integer between 1 and 4;
R is a radical of a volatile fragrance alcohol with one or more hydroxyl groups; and
R1, R2, R3, R4, and R5 are each independently selected from the group consisting of hydrogen, alkyl, hydroxyalkyl, aryl or aromatic groups;
wherein said active ingredient is the fragrance radical on the betaine ester;
and a color changing visual indicator chemistry, wherein said color changing visual indicator chemistry is selected from the group consisting of a pH indicator dye and pH adjuster, a thermochromic dye, and a polarity-sensitive dye.

21. An absorbent article comprising at least a topsheet layer, a backsheet layer and one absorbent core layer, wherein said topsheet layer, absorbent core layer and said backsheet layer each include a longitudinally directed side peripheral edge, said absorbent article including an aqueous medium-sensitive coating composition for triggered release of active ingredients from said absorbent article, said aqueous medium-sensitive coating composition being affixed to said absorbent article adjacent at least one of said longitudinally directed side peripheral edge and including a betaine ester including a functional active group and having a formula

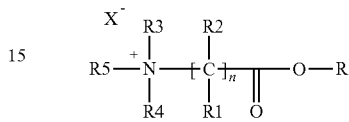

wherein
$X^-$ is an anion;
n is an integer between 1 and 4;
R is a radical of a volatile fragrance alcohol with one or more hydroxyl groups; and
R1, R2, R3, R4, and R5 are each independently selected from the group consisting of hydrogen, alkyl, hydroxyalkyl, aryl or aromatic groups;
wherein said active ingredient is the fragrance radical on the betaine ester; and
a color changing visual indicator chemistry, wherein said visual indicator chemistry is selected from at least one of the group selected from a pH indicator dye and pH adjuster, a thermochromic dye and a polarity-sensitive dye.

* * * * *